United States Patent [19]
Drumheller

[11] Patent Number: 5,897,955
[45] Date of Patent: Apr. 27, 1999

[54] MATERIALS AND METHODS FOR THE IMMOBILIZATION OF BIOACTIVE SPECIES ONTO POLYMERIC SUBSTRATES

[75] Inventor: Paul D. Drumheller, Flagstaff, Ariz.

[73] Assignee: Gore Hybrid Technologies, Inc., Flagstaff, Ariz.

[21] Appl. No.: 09/138,197

[22] Filed: Aug. 21, 1998

Related U.S. Application Data

[63] Continuation of application No. 08/660,698, Jun. 3, 1996, abandoned.

[51] Int. Cl.⁶ .......................... B32B 27/00; B32B 17/06; G01N 33/53; C12N 11/08
[52] U.S. Cl. .................. 428/422; 428/426; 428/432; 435/7.92; 435/180; 435/181
[58] Field of Search .................................. 428/426, 422, 428/432; 435/7.92, 180, 181

[56] References Cited

U.S. PATENT DOCUMENTS

| | | |
|---|---|---|
| 4,113,912 | 9/1978 | Okita . |
| 4,193,138 | 3/1980 | Okita . |
| 4,619,897 | 10/1986 | Hato et al. . |
| 4,745,160 | 5/1988 | Churchill et al. . |
| 4,885,250 | 12/1989 | Eveleigh et al. . |
| 4,929,666 | 5/1990 | Schmidt et al. . |
| 5,006,624 | 4/1991 | Schmidt et al. . |
| 5,049,403 | 9/1991 | Larm et al. . |
| 5,077,215 | 12/1991 | McAuslan et al. . |
| 5,128,170 | 7/1992 | Matsuda et al. . |
| 5,183,545 | 2/1993 | Branca et al. . |
| 5,202,227 | 4/1993 | Matusda et al. . |
| 5,203,997 | 4/1993 | Koyama et al. . |
| 5,209,850 | 5/1993 | Abayasekara et al. . |
| 5,213,898 | 5/1993 | Larm et al. . |
| 5,217,492 | 6/1993 | Guire et al. . |
| 5,240,747 | 8/1993 | Matsuda et al. . |
| 5,263,992 | 11/1993 | Guire . |

(List continued on next page.)

FOREIGN PATENT DOCUMENTS

| | | |
|---|---|---|
| 0 526 797 A1 | 2/1993 | European Pat. Off. . |
| 0 531 547 A1 | 3/1993 | European Pat. Off. . |
| WO 89/11500 | 11/1989 | WIPO . |
| WO 92/07899 | 5/1992 | WIPO . |
| WO 95/25547 | 9/1995 | WIPO . |

OTHER PUBLICATIONS

Allmer, K., Feiring, A.E. Photochemical Modification of a Fluoropolymer Surface. Macromolecules 1991; 24:5487–5488.

Boivin, P., et al. Immobilization of Perfluoroalkylated Enzymes in a Biologically Active State onto Perflex Support. Biotechnology and Applied Biochemistry 1991; 14:155–169.

(List continued on next page.)

Primary Examiner—Johann Richter
Assistant Examiner—Joseph Murray
Attorney, Agent, or Firm—Eric J Sheets

[57] ABSTRACT

The present invention is directed to support members having surfaces that are rendered hydrophilic for use as a substrate for the immobilization of bioactive species thereon. The hydrophilic surfaces are chemically stable on the support member. The surfaces are also chemically variable to provide a variety of chemically functional groups for immobilization of bioactive species thereto. The surfaces comprise polymeric surfactants attached onto the surfaces of a support member and covalently cross-linked thereon to form a first layer. Hydrophilic polymers are then attached to the first layer on the support member to form a second layer thereon. The second layer is used to enhance the hydrophilicity of a support member, as well as, to provide a substrate for immobilizing bioactive species thereto. Methods for forming the first and second layers are also provided. In addition, methods for attaching bioactive substances to the hydrophilic polymers are provided.

33 Claims, 4 Drawing Sheets

U.S. PATENT DOCUMENTS

| | | |
|---|---|---|
| 5,278,063 | 1/1994 | Hubbell et al. . |
| 5,296,510 | 3/1994 | Yamada et al. . |
| 5,308,641 | 5/1994 | Cahalan et al. . |
| 5,330,911 | 7/1994 | Hubbell et al. . |
| 5,344,455 | 9/1994 | Keogh et al. . |
| 5,352,511 | 10/1994 | Abayasekara et al. . |
| 5,354,587 | 10/1994 | Abayasekara . |
| 5,369,012 | 11/1994 | Koontz et al. . |
| 5,429,839 | 7/1995 | Graiver et al. . |
| 5,462,781 | 10/1995 | Zukowski . |
| 5,505,713 | 4/1996 | Van Antwerp . |
| 5,512,474 | 4/1996 | Clapper et al. . |
| 5,773,587 | 6/1998 | Lowe et al. . |

OTHER PUBLICATIONS

Brinkley, M. A Brief Survey of Methods for Preparing Protein Conjugates with Dyes, Haptens, and Cross–Linking Reagents. Bioconjugate Chem. 1992;3:2–13.

Chen, J.P., Kiaei, D., Hoffman, A.S. Activity of horseradish peroxide adsorbed on radio frequency glow discharge–treated polymers. J. Biomater. Sci. Polymer Edn. 1993; v5 n1/2:167–182.

Costello, C.A., McCarthy, T.J. Surface–Selective Introduction of Specific Functionalities onto Poly(tetrafluoroethylene). Macromolecules 1987; 20:2819–2828.

Danielson, N.D., Siergiej, R.W. Immobilization of Enzymes on Polytetrafluoroethylene Particles Packed in HPLC Columns. Biotechnology and Bioengineering 1981; 23:1913–1917.

Daubendiek, R.L., Calvert, J.G. The Reaction of Ozone With Perfluorinated Polyolefins. Environmental Letters 1974; v6 n4:253–272.

Dias, A.J., McCarthy, T.J. Introduction of Carboxylic Acid, Aldehyde, and Alcohol Functional Groups onto the Surface of Poly(chlorotrifluoroethylene). Macromolecules 1987; 20:2068–2076.

Forster, R.I., Bernath, F. Analysis of Urokinase Immobilization on the Polytetrafluoroethylene Vascular Prosthesis. The American Journal of Surgery Aug. 1988; 156:130–132.

Harvey, R.A., et al. Binding of Tissue Plasminogen Activator to Vascular Grafts. Thrombosis and Haemostasis (F.K. Schattauer Verlagsgesellschaft mbH Stuttgart) 1989; v61 n1:131–136.

Hirano, Y., et al. Cell–attachment activities of surface immobilized oligopeptides RGD, RGDS, RGDV, RGDT, and YIGSR toward five cell lines. J. Biomater. Sci. Polymer Edn. 1993; v4 n3:235–243.

Hyde, F.W., Hunt, G.R., Errede, L.A. Immobilization of Bacteria and *Saccharomyces cerevisiae* in Poly(Tetrafluoroethylene) Membranes. Applied and Environmental Microbiology 1991; v51 n1:219–222.

Ito, Y., et al. Cell growth on immobilized cell growth factor. 6. Enhancement of fibroblast cell growth by immobilized insulin and/or fibronectin. Journal of Biomedical Materials Research 1993; 27:901–907.

Ito, Y., Kajihara, M., Imanishi, Y. Materials for enhancing cell adhesion by immobilization of cell–adhesive peptide. Journal of Biomedical Materials Research 1991; 25:1325–1337.

Ito, Y., et al. Synthesis and nonthrombogenicity of polyetherurethaneurea film grafted with poly(sodium vinyl sulfonate). Journal of Biomedical Materials Research 1991; 25:1347–1361.

Kanazawa, S. et al. Developent of a Hydrophilic PTFE Porous Membrane Filter. Sumitomo Denki Sep. 1995; n 147:90–95.

Kasemura, T., Ozawa, S., Hattori, K. Surface Modification of Fluorinated Polymers by Microwave Plasmas. J. Adhesion 1990; 33:33–44.

Kawakami, M., Koya, H., Gondo, S. Immobilization of Glucose Oxidase on Polymer Membranes Treated by Low–Temperature Plasma. Biotechnology and Bioengineering 1988; 32:369–373.

Kobayashi, H., Ikada, Y. Covalent immobilization of proteins on to the surface of poly(vinyl alcohol) hydrogel. Biomaterials Oct. 1991; 12:747–751.

Kobos, R.K., et al. Fluorocarbon–Based Immobilization Method for Preparation of Enzyme Electrodes. Anal. Chem. 1988; 60: 1996–1998.

Kondoh, A., Makino, K., Matsuda, T. Two–Dimensional Artificial Extracellular Matrix: Bioadhesive Peptide–Immobilized Surface Design. Journal of Applied Polymer Science 1993; 47:1983–1988.

Kung, I.M. et al. Surface modifications of alginate/poly(L–l-ysine) microcapsular membranes with poly(ethylene glycol) and poly(vinyl alcohol). Biomaterials 1995; v16 n8: 649–655.

Lee, J.H., Kopecek, J., Andrade, J.D. Protien–resistant surfaces prepared by PEO–containing block copolymer surfactants. Journal of Biomedical Materials Research 1989; 23:351–368.

Lee, J.H. et al. Surface properties of copolymers of alkyl methacrylates with methoxy (polyethylene oxide) methacrylates and their application as protien–resistant coatings. Biomaterials Sep. 1990; 11:455–465.

Lin, H–B., Cooper, S.L. Polyurethane copolymers containing covalently attached RGD–Peptide: synthesis and cell adhesion studies. Mat. Res. Soc. Symp. Proc. 1992; 252:185–192.

Massia, S.P., Hubbell, J.A. Tissue engineering in the vascular graft. Cytotechnology 1992; 10:189–204.

McAuslan, B.R., et al. Cell responses to biomaterials II: Endothelial cell adhesion and growth on perfluorosulfonic acid. Journal of Biomedical Materials Research 1988; 22:963–976.

Mooney, D.J., et al. Biodegradable sponges for hepatocyte transplantation. Journal of Biomedical Materials Research 1995; 29:959–965.

Ozaki, K.C., et al. Glycoconjugate mediated endothelial cell adhesion to Dacron polyester film. Journal of Vascular Surgery 1993; v18 n3:486–494.

Ponter, A.B., Jones, W.R., Jansen, R.H. Surface Energy Changes Produced by Ultraviolet–Ozone Irradation of Poly-(Methyl Methacrylate), Polycarbonate, and Polytetrafluoroethylene. Polymer Engineering and Science Aug. 1994; v34 n16:1233–1238.

Pozniak, G., Krajewska, B., Trochimczuk, W. Urease immobilized on modified polysulphone membrane: preparation and properties. Biomaterials 1995; v16 n2:129–134.

Rucka, M., Turkiewicz, B., Zuk, J.S. Polymeric Membranes for Lipase Immobilization. JAOCS Dec. 1990; v67 n12:887–889.

Shults, M., et al. Continuous in vivo glucose analysis based on immobilized enzyme bonded to derivatized teflon membrane. Trans. Am. Soc. Artif. Intern. Organs 1979; 25:66–70.

Sipehia, R., et al. Enhanced attachment and growth of human endothelial cells derived from umbilical veins on ammonia plasma modified surfaces of PTFE and and ePTFE synthetic vascular graft Biomaterials. Biomat., Art. Cells & Immob. Biotech. 1993; v21 n4:455–468.

Sweet, G.E., Bell, J.P. Selective Chemical Etching of Poly(ethylene Terephthalate) Using Primary Amines. Journal of Polymer Science: Polymer Physics Edition 1978; 16:1935–1946.

Taylor, M.J., et al. Pepsin Immobilized on Inorganic Supports for the Continuous Coagulation of Skim Milk. Biotechnology and Bioengineering 1977; 19:683–700.

Vargo, T.G., et al. Hydrogen/Liquid Vapor Radio Frequency Glow Discharge Plasma Oxidation/Hydrolysis of Expanded Poly(tetrafluoroethylene) (ePTFE) and Poly(vinylidene Fluoride) (PVDF) Surfaces. Journal of Polymer Science: Part A: Polymer Chemistry 1991; 29:555–570.

Xie, X., Gengenbach, T.R., Griesser, H.J. Changes in wettability with time of plasma–modified perfluorinated polymers. J. Adhesion Sci. Technol. 1992; v6 n12:1411–1431.

Yan, M. et al. Photochemical Functionalization of Polymer Surfaces and the Production of Biomolecule–Carrying Micrometer–Scale Structures by Deep–UV Lithography Using 4–Substituted Perfluorophenyl Azides. J. Am. Chem. Soc. 1993; 115:814–816.

MATERIALS AND METHODS FOR THE IMMOBILIZATION OF BIOACTIVE SPECIES ONTO POLYMERIC SUBSTRATES

CROSS REFERENCE TO RELATED APPLICATIONS

This application is a continuation of application Ser. No. 08/660,698, filed Jun. 3, 1996 now abandoned.

FIELD OF THE INVENTION

The present invention relates generally to immobilized chemically functional entities. More particularly, the invention relates to materials and methods for the immobilization of bioactive species onto polymeric substrates.

BACKGROUND OF THE INVENTION

In the fields of biotechnology, biomedicine, and bioremediation, for example, bioactive species are often immobilized onto a support member to more effectively utilize the bioactive species. The term "immobilize," and its derivatives, as used herein refers to the attachment of a bioactive species directly to a support member or to a support member through at least one intermediate component. As used herein, the term "attach" and its derivatives refer to adsorption, such as, physisorption or chemisorption, ligand/receptor interaction, covalent bonding, hydrogen bonding, or ionic bonding of a polymeric substance or a bioactive species to a support member. Bioactive species include enzymes, organic catalysts, ribozymes, organometallics, proteins, glycoproteins, peptides, polyamino acids, antibodies, nucleic acids, steroidal molecules, antibiotics, antimycotics, cytokines, carbohydrates, oleophobics, lipids, pharmaceuticals, and therapeutics, for example. Cells, such as, mammalian cells, reptilian cells, amphibian cells, avian cells, insect cells, planktonic cells, cells from non-mammalian marine vertebrates and invertebrates, plant cells, microbial cells, protists, genetically engineered cells, and organelles, such as mitochondria, are also bioactive species. In addition, non-cellular biological entities, such as viruses, virenos, and prions are considered bioactive species.

There are various materials suitable for use as a support member for immobilizing bioactive species. Examples of these materials include hydrocarbon polymers, fluorocarbon polymers, ceramics, and metals. Of these materials, polytetrafluoroethylene and porous polytetrafluoroethylene, are of particular interest as support members. Polytetrafluoroethylene (PTFE) is a hydrophobic fluorocarbon polymer well known to have exceptional resistance to solvent and chemical attack. Porous polytetrafluoroethylene can be made in a variety of ways. For example, coextrusion of a polytetrafluoroethylene extrudate with a readily vaporizable material, such as naptha, forms a material from which the readily vaporizable material is ultimately removed to render the material porous (See U.S. Pat. No. 3,281,511, which is incorporated herein by reference). Expanded polytetrafluoroethylene (ePTFE) or stretched polytetrafluoroethylene are porous fluorocarbon polymer materials characterized primarily by a multiplicity of interconnecting voids defined by nodes and fibrils of polytetrafluorethylene material. Expanded PTFE materials, including ePTFE membranes and films described hereinbelow, may be made according to the teachings of U.S. Pat. Nos. 3,953,566, 3,962,153, 4,096, 227, 4,187,390, and 4,902,423, each of which is incorporated herein by reference. In general, porous PTFE materials are chemically stable and very biocompatible. The materials have easily controlled pore sizes with large surface area/volume ratios, good mechanical strength, and good resistance to fouling, among other properties. Accordingly, these materials are attractive as support members for the immobilization of bioactive species.

Several methods for immobilizing bioactive species onto fluorocarbon polymers, such as PTFE, porous PTFE, or hydrocarbon polymeric materials have been taught in the literature. These methods include, for example, chemical modifications of the polymeric material to form chemically reactive groups thereon for covalent bonding of a bioactive species to the material, adsorption of a bioactive species to the polymeric material, and modifying the polymeric material and/or a bioactive species with compatibilizers, surfactants, or wetting agents to alter their surface energies. As described below, there are difficulties with each of these methods.

Due to the extreme chemical inertness of the backbone of fluorocarbon polymers and many hydrocarbon polymers, only highly energetic classes of reactions can successfully alter the backbone of these materials to produce chemically reactive organic moieties thereon. When chemically reactive organic moieties are formed along the backbone of a fluorocarbon or hydrocarbon polymer, bioactive species can be attached to the moieties. For example, enzymes have been chemically attached onto ammonia plasma-treated fluoropolymer surfaces using ammonia plasma and glutaraldehyde (See M. Kawakami, H. Koya, and S. Gondo, "Immobilization of glucose oxidase on polymer membranes treated by low-temperature plasma," Biotech. Bioeng., 32: 369, (1988)), or aminosilane and glutaraldehyde (J. M. Taylor, M. Cheryan, T. Richardson, and N. F. Olson, "Pepsin immobilized on inorganic supports for the continuous coagulation of skim milk," Biotech. Bioeng., 19: 683 (1977), for example). Representative examples of these highly energetic reactions include, thermal decomposition (U.S. Pat. No. 5,296,510, issued to Shigeru et al.), irradiation with electrons, gamma rays, radio waves, microwaves (T. Kasemura, S. Ozawa, K. Hattori, "Surface Modification of Fluorinated Polymers by Microwave Plasmas," J. Adhesion, 33: 33 (1990); Commonwealth Scientific and Industrial Research Organisation in PCT/AU89/00220; Y. Ito, Y. Iguchi, T. Kashiwagi, Y. Imanisihi, "Synthesis and nonthrombogenicity of polyetherurethaneurea film grafted with poly(sodium vinyl sulfonate)," J. Biomed. Mater. Res., 25: 1347 (1991); and Y. Ito, M. Kajihara, Y. Imanishi, "Materials for enhancing cell adhesion by immobilization of cell adhesive peptide," J. Biomed. Mater. Res., 25: 1325 (1991)), or UV light (K. Allmer, A. E. Feiring, "Photochemical Modification of a Fluoropolymer Surface," Macromolecules, 24: 5487 (1991); A. B. Pointer, W. R. Jones Jr., R. H. Janse, "Surface energy changes produced by ultraviolet-ozone irradiation of poly (methyl methacrylate), polycarbonate, and polytetrafluoroethylene," Polym. Eng. Sci., 34: 1233 (1994)), glow discharge irradiation (R. Sipehia, G. Martucci, M. Barbarosie, C. Wu, "Enhanced Attachment of and Growth of Human Endothelial Cells Derived from Umbilical Veins on Ammonia Plasma Modified Surfaces of PTFE and ePTFE Synthetic Vascular Graft Biomaterials," Biomat. Art. Cells Immob. Biotech., 21:455 (1993)), and redox reactions with strong nucleophiles such as sodium or potassium aryloxides (C. A. Costello, T. J. McCarthy, "Surface-selective Introduction of Specific Functionalities onto Poly (tetrafluoroethylene)," Macromolecules, 20: 2819 (1987); A. J. Dias, T. J. McCarthy, "Introduction of carboxylic acid, aldehyde, and alcohol functional groups onto the surface of poly(chlorotrifluoroethylene)," Macromolecules, 20: 2068

(1987); G. E. Sweet, J. P. Bell, "Selective chemical etching of poly(ethylene terephthalate) using primary amines," J. Polym. Sci. Phys. Ed., 16: 1935 (1978); and H. B. Lin, S. L. Cooper, "Polyurethane copolymers containing covalently attached RGD-peptide," Mat. Res. Soc. Symp. Proc., 252: 185 (1992)), or ozone (R. L. Daubendiek, J. G. Calvert, "The Reaction of Ozone with Perfluorinated Polyolefins," Environ. Lett., 6: 253 (1974)).

These high-energy modifications can be highly destructive to polymeric materials, however. With PTFE and porous PTFE, for example, high-energy modifications of the fluorocarbon backbone often leads to uncontrolled surface erosion of the material, depolymerization of the perfluorocarbon backbone (A. B. Pointer, W. R. Jones Jr., R. H. Jansen, "Surface Energy Changes Produced by Ultraviolet-ozone Irradiation of Poly(methyl methacrylate), Polycarbonate, and Polytetrafluoroethylene," Polym. Eng. Sci., 34: 1233 (1994)), reduction in the strength of the polymer substrate (S. Kanazawa, T. Takiguchi, A. Nishimora, T. Morita, and A. Uno, "Development of a Hydrophilic PTFE porous membrane filter," Sumitomo Denki; 147:99 (Sept., 1995), and loss of defined fibrillar structure of porous expanded PTFE (U.S. Pat. No. 5,462,781, issued to Zukowski).

Furthermore, high energy modifications to hydrocarbon polymers and fluorocarbon polymers, such as PTFE or porous PTFE, often produce reactive compositions on the hydrocarbon or fluorocarbon backbone that have an undeterminable surface density, chemical identity, and chemical stability (X. Xie, T. R. Gengenbach, and H. J. Griesser, "Changes in wettability with time of plasma modified perfluorinated polymers," J. Adhesion Sci. Technol., 6:1411 (1992)). In addition, the modification of the hydrocarbon or perfluorocarbon backbone may be spatially uneven, with microscopic or macroscopic areas of the polymer remaining unmodified. At best, these surface compositions can only be empirically determined and so may be only partially known.

With a hydrophobic porous polymer, such as ePTFE or porous polyethylene, for example, modification of the backbone may be limited to the outer layers of the porous material, with the inner pore structures remaining mostly or completely unmodified. As a result, the unmodified regions of the polymer support member remain hydrophobic and so do not readily support wetting with high surface tension fluids. In the absence of such wetting, continuous passage of high surface tension fluids through the support member for mass transport of reactants or nutrients to and from an immobilized bioactive species cannot be established or maintained. Intermittent or incomplete passage of high surface tension fluid phases in a porous polymer support member can lead to channeling of the high surface tension fluid through only portions of the porous material, resulting in reduced efficiency. Moreover, these unmodified areas cannot be immobilized with bioactive species, resulting in inefficient use of the high surface area of the porous material.

Due to these limitations, modification of the backbone of a hydrocarbon or fluorocarbon polymer support member with a high energy reaction is most often an unsuitable method for immobilization of bioactive species.

As an alternative to these chemical modifications of polymeric surfaces, nonchemical methods have been employed to attach bioactive species to hydrocarbon and fluorocarbon support members. In the simplest method, a bioactive species is immobilized onto the surfaces of a fluorocarbon polymer via simple physicochemical adsorption. For example, M. Rucha, B. Turkiewicz, and J. S. Zuk, "Polymeric membranes for lipase immobilization," J. Am. Oil Chem. Soc., 67: 887 (1990) and Shults, M. et al., "Continuous In Vivo Glucose Analysis Based On Immobilized Enzyme Bound To Derivatized Teflon Membrane," Trans. ASAIO, 25: 66 (1979) each teach enzyme physisorption onto ePTFE. However, physisorption of bioactive species is often kinetically and thermodynamically unstable, highly reversible, and competitively displaced by solution phase reactants, products, or nutrients. In addition, physisorption may alter or damage the bioactive species. Thus, physisorption of bioactive species to hydrocarbon polymer or fluorocarbon polymer support members is not usually a suitable immobilization technique. Furthermore, the hydrophobic properties of a porous hydrocarbon polymer or porous fluorocarbon polymer support member, such as ePTFE, often prevent physisorption of a bioactive species in the inner pore structures of the support member.

In another non-chemical immobilization scheme, bioactive species such as cells have been immobilized to porous PTFE support members. For example, bacteria and yeast cells have been immobilized in PTFE fibril matrices using an emulsion of PTFE and surfactants (F. W. Hyde, G. R. Hunt, and L. A. Errede, "Immobilization of bacteria and *Saccharomyces cerevisiae* in poly(tetrafluoroethylene) membranes," Appl. Environ. Microbial., 57: 219 (1991)) The surfactant is necessary to ensure for the presence of a continuous water phase throughout the emulsion in order to allow diffusion of nutrients to cells immobilized within the porous regions of the material. This method for immobilization of cells in the porous matrices of a fluorocarbon polymer is quite harsh, however, as many surfactants are cytotoxic. As a result, this method is not generally applicable to all cell types because the reaction conditions are often toxic to cell types such as plant or mammalian cells. In addition, the surfactant may initially obstruct some or all of the void space of the pores in such a porous support member. Lastly, the surfactant may leach from the support member with time. This often presents a toxic environment to the immobilized cells or channelling of nutrients, resulting in a heterogeneous distribution of cells within the porous support member. Accordingly, this is often an unsuitable method for the immobilization of bioactive species.

In yet another non-chemical method, mammalian cells have been immobilized within ePTFE support members by forcing the cells into the pores of the material by hydrostatic pressure (University of Washington, PCT/US95/03735). However, cell viability is often low due to mechanical shearing forces produced during the process. In addition, the ePTFE remains hydrophobic and mass transport of liquid water across the thickness of the material may remain low, resulting in suboptimal transport of nutrients to the immobilized cells.

In an attempt to improve the immobilization of bioactive species adsorbed onto hydrocarbon or fluorocarbon polymer support members, the hydrophobicity of the surfaces of such polymer support members can be modified with hydrophilic surface active agents, or surfactants. Hydrophobic surfaces are low energy surfaces that are readily wetted by low surface tension fluids, such as low molecular weight hydrocarbons or alcohols, and most low molecular weight organic solvents, such as benzene, acetone, toluene, and dioxane, etc. Hydrophilic surfaces, on the other hand, are high energy surfaces that are readily wetted by high surface tension fluids. Examples of high surface tension fluids include, but are not limited to, liquid water, aqueous salt and protein solutions, dimethyl formamide, dimethyl sulfoxide, glycerol, hexamethyl phosphorictriamide, formamide, and glycol, for example. In these methods, surfactants were physisorbed onto the surfaces of a polymeric hydrocarbon or fluorocarbon support member. When a surfactant is applied to the surfaces of a hydrophobic polymeric support member, the surface energy of the support member is usually increased. The increased surface energy of the support member often facilitates attachment of a bioactive species to the support member. For example, U.S. Pat. Nos. 5,077,215, issued to McAuslan et al., 5,183,545, issued to Branca et al., and 5,203,997 issued to Koyama et al., teach the adsorption of anionic and nonionic fluorocarbon surfactants to the surface of fluorocarbon support members to modify their hydrophobicity. As a result, the normally hydrophobic surface of the polymer was rendered more hydrophilic. This was followed by physisorption of a bioactive species onto the surfactant-modified polymer surface.

In similar methods, the adsorption of surfactants onto polymeric support members is taught wherein bioactive species are subsequently bound to the adsorbed surfactants. For example, U.S. Pat. No. 5,263,992, issued to Guire et al., teaches adsorption of polymeric chains to a support member, to which biomolecules are attached through a photoactive agent. In this manner, bioactive species were more readily immobilized onto the support member than if directly immobilized onto the underlying hydrophobic polymer surface. Alternatively, the bioactive species may be covalently bonded directly to the surfactant rather than physisorbed thereto (See also, U.S. Pat. No. 4,619,897, issued to Hato et al., for example).

In these methods, the presence of a surfactant provided for a surface having a hydrophilicity that initially enhanced the immobilization of bioactive species. For porous support members, the surfactant also initially provided continuous water phases through the pores of the support member. As discussed in greater detail below, immobilization of bioactive species with surfactants is usually unstable over time, however.

The physicochemical stability of the immobilized bioactive species is another concern when bioactive species are immobilized with surfactants. The adsorption of surfactants to a polymeric support member can serve to enhance the strength of biospecies adsorption, but the biospecies may desorb from the surfactant-treated surface nevertheless. In order to improve the retention of the bioactive species on a support member, U.S. Pat. No. 4,885,250, issued to d'Eveleigh, teaches modifying biological ligands themselves with surfactants prior to physisorption of the surfactant onto the support member. However, modification of bioactive species with surfactants prior to physisorption onto hydrophobic polymer surfaces may dramatically impact the bioactivity of the bioactive species. For example, the enzyme lactate dehydrogenase was admixed with surfactants and physisorbed onto PTFE microparticles resulting in a drop in enzymatic activity of 96% (N. D. Danielson, and R. W. Siergiej, "Immobilization of enzymes on polytetrafluoroethylene particles packed in HPLC columns," Biotech. Bioeng., 23: 1913 (1981)). In another example, the enzyme urease was modified with perfluoroalkyl chains and then physisorbed onto ePTFE resulting in an initial drop in enzymatic activity of 10–18% and poor overall enzymatic stability (R. K. Kobos, J. W. Eveleigh, M. L. Stepler, B. J. Haley, S. L. Papa, "Fluorocarbon-Based Immobilization Method for Preparation of Enzyme Electrodes," Anal. Chem., 60: 1996 (1988)). Additionally, adsorbed surfactant-modified bioactive species may remain molecularly motile and may migrate and cluster on the surface of a hydrocarbon polymer or fluorocarbon polymer support member. This effect may be accelerated with the application of cosolvents, changes in pH, or elevated temperatures, such as autoclaving, often leading to significant reorganization of the bioactive species on the surface of the support member. This can cause a loss in wetting potential of the support member with high surface tension liquids and/or uneven spatial immobilization of a bioactive species (U.S. Pat. No. 5,352,511, issued to Abaysekara et al.). As a result of these limitations, modification of a bioactive species with a surfactant prior to immobilizing the bioactive species to a hydrophobic support member is most often an unsuitable method.

Surfactants, whether physisorbed onto a hydrophobic support member or attached to a bioactive species and then adsorbed to a hydrophobic support member, are subject to desorption. For example, R. I. Foster, et al. in "Analysis of Urokinase Immobilization on the polytetrafluoroethylene vascular prosthesis," Am. J. Surg., 156: 130 (1988) teach adsorption of the hydrocarbon surfactant tridodecylmethylammonium chloride onto the surfaces of ePTFE followed by immobilization of the enzyme urokinase to the surfactant. The adsorption was unstable and the enzyme/surfactant construct was eventually displaced. An additional limitation with this immobilization method is the tendency for the surfactant to leach into the solute phase, often with undesired consequences, such as contamination or inactivation of desired products or the bioactive species. Accordingly, immobilization of bioactive species onto a hydrophobic support member with a surfactant is usually unstable, short-lived, and potentially harmful to the bioactive species.

The stability of surfactant adsorption on a hydrocarbon or fluorocarbon polymer surface can be enhanced by increasing the molecular weight of the surfactant (J. H. Lee, J. Kopecek, J. D. Andrade, "Protein-Resistant Surfaces Prepared by PEO-Containing Block Copolymer Surfactants," J. Biomed. Mater. Res., 23: 351 (1989)) or by lowering the molecular entropy of the surfactant (J. H. Lee, P. Kopeckova, J. Kopecek, J. D. Andrade, "Surface Properties of Alkyl Methacrylates with Methoxy (polyethylene oxide) Methacrylates and Their Application as Protein-resistant Coatings," Biomaterials, 11: 455 (1990)). Either of these approaches can be accomplished by producing surfactants with branched or comb-like hydrocarbon chains, rather than linear hydrocarbon chains, for example. However, the stability of the adsorbed surfactant may still be transient, albeit much stronger, and may desorb from the support surface nevertheless, rendering this technique potentially unfeasible for long term applications.

In another method to reduce surfactant desorption or surfactant motility, adsorbed surfactant chains may be covalently cross-linked to adjacent adsorbed surfactant chains, producing new surface-bound planar molecules. The resulting planar molecules are of very high molecular weight and have greatly reduced molecular entropy. This type of cross-linking dramatically reduces the incidence of desorption or surface migration of the surfactant. For example, U.S. Pat. Nos. 4,929,666, issued to Schmidt et al., and 5,006,624, issued to Schmidt et al. teach adsorbing copolymers of fluoroalkyl acrylates and carboxylic vinyls, respectively, onto fluorocarbon polymer surfaces, followed by surface cross-linking of adsorbed carboxylic moieties to produce a coating highly stable to surface reorganization or to desorption. In another example, a hydrophilic fluorocarbon polymer of tetrafluoroethylene-co-vinyl alcohol was adsorbed and chemically cross-linked to itself using a polyether bisoxirane cross-linker (U.S. Pat. No. 5,354,587, issued to Abaysekara). In another example, a hydrophilic hydrocarbon polymer of polyvinyl alcohol was adsorbed and cross-linked to itself using a dialdehyde cross-linker (U.S. Pat. Nos. 4,113,912 and 4,193,138, both issued to Okita). This resulted in the ePTFE surface being rendered wettable with liquid water and the adsorbed copolymer molecules being highly resistant to desorption or to surface migration. However, these hydrophilic surfaces have limited or greatly reduced numbers of chemically functional groups to which additional polymers or bioactive species can be attached. If the adsorbed copolymer layer is deficient in the desired number or identity of chemically functional groups it possesses, then the capacity of the adsorbed copolymer or surfactant layer to immobilize bioactive species will always remain suboptimal. Accordingly, this type of cross-linking of adsorbed surfactant or copolymer molecules on hydrocarbon or fluorocarbon polymer support members is often unsuitable for the subsequent immobilization of bioactive species.

A support member having chemically stable and chemically variable hydrophilic polymeric surfaces attached thereto as a substrate upon which bioactive species are stably and efficiently immobilized would be useful. Such a construction would enable a practitioner to increase the number and/or variety of immobilized bioactive species. A practitioner would also be able to select a conjugation scheme for immobilization of a bioactive species that is best suited for the particular bioactive species.

SUMMARY OF THE INVENTION

As described in the Background Section, prior methods for the immobilization of bioactive species to support members comprised of hydrocarbon polymer or fluorocarbon polymer based materials are problematic. The present invention resolves the above-described problems with a construction that eliminates chemical modifications of the support member, as well as, the necessity to take preventative measures to reduce the desorption of immobilized bioactive species from the support member and the necessity to modify the bioactive species with surfactants prior to immobilization. The present invention provides a support member with hydrophilic surfaces to which bioactive species are readily immobilized. The hydrophilic surfaces of the construction are chemically stable. The number and type of chemically functional groups of the hydrophilic surfaces can be varied. The ability to vary the chemically functional groups of the hydrophilic surfaces permits a practitioner to increase the number and/or variety of chemically functional groups to which bioactive species can be immobilized. The present invention also permits a practitioner to select a conjugation scheme for immobilization of bioactive species that best preserves the bioactivity and stability of the immobilized bioactive species.

In the present invention, adsorption of a polymeric surfactant onto a support member, followed by cross-linking chains of the surfactant polymers together in situ provides a physically and chemically stable substrate, or first layer, to which a hydrophilic polymer is subsequently attached forming a second layer thereon. Preferably, the hydrophilic polymer of the second layer is covalently attached to the cross-linked polymeric surfactant of the first layer. The hydrophilic polymer of the attached second layer has chemically functional groups through which bioactive species are immobilized. The hydrophilic polymer of the second layer is selected to provide one or more specific type of chemically functional group for immobilization of bioactive species. Once a bioactive species is attached to the second layer, the result is a support member having hydrophilic surfaces that are physically stable and chemically variable to which bioactive species are stably immobilized (See FIG. 1).

If desired, a plurality of layers of hydrophilic polymers may be attached to the first layer and bioactive species attached to at least one of the layers (See FIG. 2). In addition to serving as a substrate for immobilization of a bioactive species, additional layers of hydrophilic polymers can serve to enhance the hydrophilic properties of the construction and/or as a permeable protective covering for the bioactive species.

Alternatively, bioactive species can be immobilized directly to chemically functional groups of the first layer, as illustrated in FIG. 3, or to excess chemically functional groups of the cross-linking agent attached to the first layer, as illustrated in FIG. 4.

Referring to FIG. 1, one embodiment of the present invention (10) is directed to a material having immobilized bioactive species comprising a support member (12); a first layer (14) comprised of at least one species of a polymeric surfactant attached to the support member and cross-linked together in situ; a second layer (18) comprised of at least one species of a hydrophilic polymer attached to the first layer; and at least one type of bioactive species (19) attached to the second layer.

While the present invention has wide applications, it is particularly suitable for immobilization of insulin secreting pancreatic islet cells or genetically engineered insulin secreting cells. Immobilization of such cells may be useful for facilitating transplantation and/or implantation of the cells into a recipient as a means for treating or ameliorating various diseases, such as neuro-endocrine diseases, including diabetes mellitus, neurological diseases, including Parkinson's Disease, metabolic deficiency diseases, including Hurler's Disease, for example. The present invention is also suitable for the immobilization of renal epithelial or interstitial cells for use in renal failure therapy. Of particular interest in this regard is the use the present invention in the form of a membrane barrier for the encapsulation of immobilized therapeutic cells. Another use of the present invention is for the immobilization of hepatocytes for construction of extracorporeal liver assist devices. Yet another use is the immobilization of autologous vascular endothelial cells onto a synthetic vascular graft or onto a polymer coated metallic stent for improvement of vascular patency. Further uses include the immobilization of anti-coagulant factors, such as heparin, heparan sulfate, tPA, protein S, various lysine compounds, urokinase, protein C, etc. onto a synthetic vascular graft or onto a polymer coated metallic stent for improvement of vascular patency; immobilization of pro-coagulant factors, such as tissue factor, von Willebrand factor, factor XIII, kininogen, thrombin, etc.; the immobilization of adhesion-dependent or adhesion-independent cell lines comprising genetically engineered cells for use in genetic therapy; the immobilization of adhesion-dependent or adhesion-independent cell lines for use in transplantation therapy; the immobilization of pro-adhesive ligands, such as the tripeptide Arg-Gly-Asp, collagens, and fibronectin, for example, in order to promote adhesion of cellular bioactive species, the immobilization of anti-adhesive ligands, such as dextran, albumin, and polyethylene glycol, for example, in order to reduce non-specific cellular adhesion to support members; and the immobilization of bacteria or yeast cells for use in bioremediation and biotechnology.

In other applications, enzymes, catalytic antibodies, or phase transfer catalysts may be employed in the present invention to perform biocatalytic reactions, such as biosensing and enzyme affinity chromatography. In addition, proteins, peptides, carbohydrates, antibodies, lectins, or lipids may be utilized in the present invention to prepare ligand affinity or immunomatrix chromatography columns for detection or separation of products from a liquid stream. Another use of the present invention is as a solid substrate upon which the synthesis of peptides or drugs can be conducted. In many of these uses, the present invention is in the form of a permeable, or semi-permeable, membrane barrier that provides a continuous solvent phase across the barrier, such as for transport of gases, nutrients, or reaction products.

The present invention is also directed to methods for rendering the surfaces of a hydrophobic support member hydrophilic by elevating the surface energy of these materials to support wetting and spreading of high surface tension fluids thereon. The present invention is also directed to methods for stably immobilizing bioactive species to the hydrophilic surfaces formed on the support member.

DETAILED DESCRIPTION OF THE INVENTION

The present invention is directed to polymeric materials, referred to herein as support members, having a substrate attached thereto comprised of layers of chemically stable and chemically variable hydrophilic polymers to which bioactive species are stably immobilized. Optionally, metallic or ceramic materials can be used in the present invention as support members.

Figure 5:
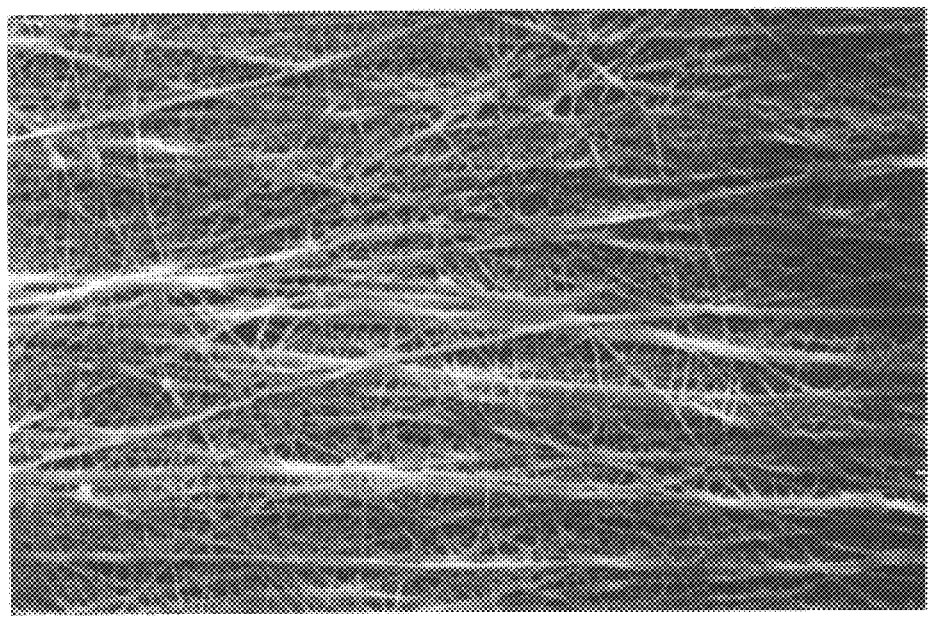
FIG. 5 is a scanning electron micrograph of the microstructure of a porous polytetrafluoroethlyene support member having a bioactive species immobilized thereon.

For porous support members, the present invention also permits bioactive species to be readily immobilized on the surfaces defining the porous regions of the support member without significantly reducing the porosity of the support member (See FIG. 5, for example). The result is a support member having surfaces rendered hydrophilic and wettable with high surface tension fluids throughout its bulk to which at least one type of bioactive species is immobilized.

In the preferred embodiment of the present invention, the construction is assembled from the following components: a support member comprised of a polymeric material; a first layer comprised of at least one species of a polymeric surfactant, or a multifunctional copolymer, comprised of at least one domain that has a physicochemical affinity for the support member to allow physicochemical adsorption of the polymer onto the surface of the support member and at least one other domain that is chemically reactive to allow covalent cross-linking with a suitable cross-linking agent; a suitable cross-linking agent; a second layer comprised of one or more hydrophilic surfactants, homopolymers, or copolymers that contain chemically functional groups capable of reacting with unconsumed free cross-linking groups from the first layer and have additional groups to provide increased hydrophilicity to the construction and for subsequent attachment of bioactive species thereto; and a bioactive species attached to the chemically functional groups of the second layer.

Suitable materials for a hydrophobic polymeric support member include, but are not limited to, polytetrafluoroethylene, expanded polytetrafluoroethylene, porous polytetrafluoroethylene, fluorinated ethylene propylene, hexafluroropropylene, polyethylene, polypropylene, nylon, polyethyleneterephthalate, polyurethane, silicone rubber, polystyrene, polysulfone, polyester, polyhydroxyacids, polycarbonate, polyimide, polyamide, polyamino acids, regenerated cellulose, or proteins, such as silk, wool, and leather. Expanded, or porous, polytetrafluoroethylene (ePTFE) is particularly preferred. Methods of making porous polytetrafluoroethylene materials are described in U.S. Pat. Nos. 3,953,566 and 4,187,390, both issued to Gore, each of which is incorporated herein by reference.

Though the present invention is primarily directed to constructions made with support members that are hydrophobic, some non-hydrophobic materials may also be suitable for use in the present invention. Suitable materials for hydrophilic support members include, but are not limited to, cellulosics, agarose, alginate, polyhydroxyethylmethacrylate, polyvinyl pyrrolidone, polyvinyl alcohol, polyallyamine, polyallylalcohol, polyacrylamide, and poly acrylic acid, for example. Lastly, certain metals and ceramics may be suitable materials or use as support members in the present invention. Suitable metals for support members include, but are not limited to, titanium, stainless steel, gold, silver, rhodium, zinc, platinum, rubidium, and copper, for example. Suitable materials for ceramic support members include, but are not limited to, silicone oxides, aluminum oxides, alumina, silica, hydroxyapapitites, glasses, calcium oxides, polysilanols, and phosphorous oxide, for example.

To construct the present invention, a first layer is formed on a support member by adsorbing a polymeric surfactant to the surfaces of the support member followed by cross-linking the surfactant to itself in situ. For a porous support member, the first layer is optionally adsorbed to material defining the porous void spaces of the support member as well. For example, a solution comprised of a polymeric surfactant dissolved in a suitable solvent at a concentration of about 0.001% to about 99.9%, preferably about 0.25% to about 5%, is initially adsorbed onto the surfaces and optionally into the porous spaces of a porous support member simply by dipping the support member in the solution for about 0.05 minutes to about 20 minutes, to permit physisorption of the surfactant to the surfaces of the support member. Suitable materials for the first layer include, but are not limited to, polyvinyl alcohol, polyethylene glycol, polypropylene glycol, dextran, agarose, alginate, polyacrylamide, polyglycidol, poly(vinyl alcohol-co-ethylene), poly(ethyleneglycol-co-propyleneglycol), poly(vinyl acetate-co-vinyl alcohol), poly(tetrafluoroethylene-co-vinyl alcohol), poly(acrylonitrile-co-acrylamide), poly(acrylonitrile-co-acrylic acid-co-acrylamidine), polyacrylic acid, poly-lysine, polyethyleneimine, polyvinyl pyrrolidone, polyhydroxyethylmethacrylate, and polysulfone, and their copolymers, either alone or in combination. Preferred copolymers for formation of the first layer are copolymers comprised of at least one moiety capable of physicochemically adsorbing to the support member, a moiety capable of chemical modification with a suitable agent, and a moiety capable of interacting with high surface tension fluids. These moieties may be selected such that one moiety fulfills all of these three roles simultaneously, fulfills two roles, or fulfills only one role. Suitable solvents for this purpose include, but are not limited to, methanol, ethanol, isopropanol, tetrahydrofuran, trifluoroacetic acid, acetone, water, dimethyl formamide (DMF), dimethyl sulfoxide (DMSO), acetonitrile, benzene, hexane, chloroform, and supercritical carbon dioxide.

When using a hydrophobic support member and the polymer chosen for the first layer dissolves in only high surface tension solvents, the hydrophobic support member should be prewetted with a miscible solvent having a low surface tension to effect adsorption of the polymer for the first layer. For porous support members, excess adsorbed surfactant may be rinsed from the surface of the support member using fresh solvent to prevent bulk deposited surfactant from partially blocking pores of the support member. Though optional, this step is preferred in order to ensure that the pores of a porous support material, such as ePTFE, are not obstructed with surfactant.

The polymeric surfactant of the first layer is covalently cross-linked to itself in situ using a suitable cross-linking agent to produce surface-bound planar molecules of extremely high molecular weight. These very high molecular weight molecules serve to greatly reduce or eliminate the potential for desorption or migration of the surfactant. Suitable reagents for use in cross-linking the polymeric surfactant in situ are compounds comprised of at least two chemically functional groups, either homofunctional or heterofunctional, that include, but are not limited to, aldehydes, epoxides, acyl halides, alkyl halides, isocyanates, amines, anhydrides, acids, alcohols, haloacetals, aryl carbonates, thiols, esters, imides, vinyls, azides, nitros, peroxides, sulfones, and maleimides, dissolved in solvents that wet the adsorbed layer. Solvents suitable for dissolving the cross-linking reagent include, but are not limited to, acetone, water, alcohols, tetrahydrofuran (THF), dimethyl sulfoxide (DMSO), dimethyl formamide (DMF), benzene, acetonitrile, and dioxane. Other reagents include, but are not limited to, free radicals, anions, cations, plasma irradiation, electron irradiation, and photon irradiation. One preferred cross-linking agent is glutaraldehyde, preferably using a catalyst of HCl, preferably dissolved in water.

Figure 4:
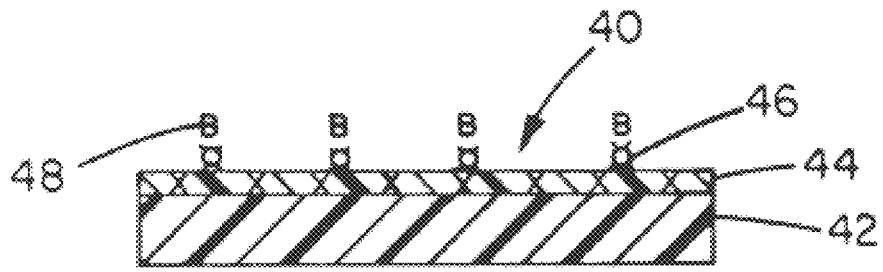
FIG. 4 illustrate a cross-section of the present invention (40) having a first layer (44) attached to a support member (42) wherein bioactive species (48) are immobilized to the first layer through excess chemically functional groups of the cross-linking agent. The letter "x" indicates that the constituents of the first layer are cross-linked together. The symbol "¤" (46) represents excess chemically functional groups of the cross-linking agent. The letter "B" (48) in FIG. 4 represents a bioactive species (48).
Figure 6:
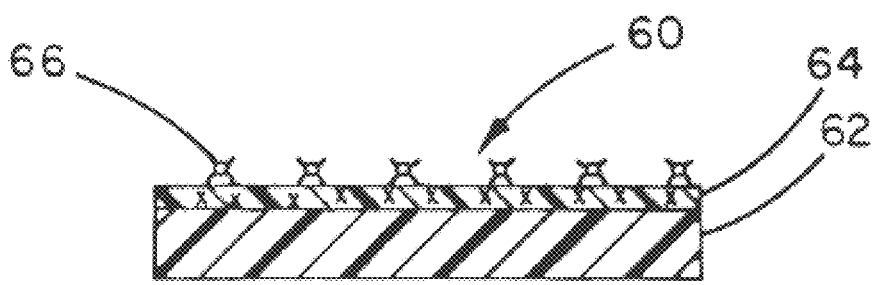
FIG. 6 illustrates a cross-section of the present invention (60) having a first layer (64) attached to a support member (62) wherein the constituents of the first layer are cross-linked together and excess chemically functional groups of the cross-linking agent are present. The letter "x" indicates that the constituents of the first layer are cross-linked together. The symbol "¤" (66) represents excess chemically functional groups of the cross-linking agent.

Regardless of which cross-linking agent is used, the cross-linking agent is preferably added in excess, i.e, in such an amount that sufficient unreacted chemically functional groups of the cross-linking reagent will be present to serve as points of attachment for the second layer following the cross-linking step (See FIG. 6). Thus, the cross-linking scheme fulfills two roles. In one role, cross-linking forms surface-bound planar molecules of extremely high molecular weight. In another role, cross-linking provides chemically functional groups to which the second layer is subsequently attached. Bioactive species are then attached to unreacted chemically functional groups of the cross-linking agent (See FIG. 4).

In an alternative embodiment, the polymeric surfactant of the first layer can be attached to the support member with methods that do not use a chemical cross-linking agent. For example, polymeric surfactants containing numerous nitrile groups can spontaneously self assemble into a stable conformal coating when adsorbed onto the support member. The stability of the coating is derived from the physical cross-linking of neighboring polymer chains via cyano polar interactions. In another example, the polymeric surfactant may be physically cross-linked using a suitable agent via acid-base coacervation, e.g., a first layer formed of a cationic polymeric surfactant can be physically cross-linked by the application of an anionic agent. In addition, an amphoteric polymeric surfactant may spontaneously self assemble into a conformal coating via internal acid-base coacervation. In yet another example, the Minnesota Mining and Manufacturing Company, in PCT/US91/07686, teach the application of a hydrophilic polyvinyl alcohol layer that is non-covalently cross-linked via inter- and intrachain polymer crystallization.

The degree of cross-linking of the first layer may be assessed by Fourier Transform Infrared Spectroscopy (FTIR). For example, with FTIR, the free hydroxyl groups of polyvinyl alcohol (PVA) are detectable before cross-linking at approximately 3349 $cm^{-1}$. After cross-linking, the peak shifts to approximately 3383 $cm^{-1}$ and decreases in height. As a positive internal control, an FTIR peak at approximately 2942 $cm^{-1}$ due to the CH2 groups does not change position or height as a result of cross-linking. A shift in the hydroxyl group (OH) peak position from approximately 3349 $cm^{-1}$ to approximately 3383 $cm^{-1}$ with a decrease in peak height is an indication of the amount of PVA that has become cross-linking in the formation of the first layer.

The extent to which free, or excess, aldehyde groups of a cross-linking agent, such as glutaraldehyde, are present in the first layer following the cross-linking step can also be detected using FTIR. For example, when an article of the present invention having a first layer of PVA extensively cross-linked with glutaraldehyde is steam sterilized, the article usually has FTIR peaks at about 1590 $cm^{-1}$ and about 1690 $cm^{-1}$. These peaks are believed to represent excess aldehyde groups of the first layer and its partial hydrolysis products by the exposure to steam. A similar article having a first layer that is briefly exposed to a glutaraldehyde cross-linking agent does not usually have an FTIR peak at 1590 $cm^{-1}$. Accordingly, the degree to which a first layer is contains excess chemically functional groups can be assessed by comparing the ratio of an FTIR peak at about 1690 $cm^{-1}$ to an FTIR peak at about 1590 $cm^{-1}$.

FTIR can also be used to detect the presence of a second layer attached to a first layer cross-linked with glutaraldehyde. For example, an article of the present invention having a second layer of PVA attached to a first layer of PVA will have strong FTIR peaks at about 2950 $cm^{-1}$ and at about 3350 $cm^{-1}$. These peaks represent signal from the hydrocarbon backbone and the free hydroxyl groups of the PVA, respectively, from both the first and second layers. The absence of an FTIR peak at about 1590 $cm^{-1}$ and about 1690 $cm^{-1}$ indicates that substantially all of the aldehyde groups of the glutaraldehyde cross-linking agent were consumed during attachment of the second layer to the excess aldehyde groups of the first layer.

In addition, a first or second layer of poly(lysine) on a support member may be detected by X-ray photoelectron spectroscopy (XPS). For example, the addition of amino groups (NH2) onto the surface can be detected by the measurement of nitrogen. Nitrogen is usually not present in either hydrocarbon or fluorocarbon support members of the present invention. Similarly, the immobilization of cell adhesion peptides, such as the Arg-Gly-Asp amino acid sequence, onto a first or second layer of PVA, for example, can be detected by XPS.

In the case of a three-dimensional device, such as a foam or sponge, the presence of a hydrophilic layer attached directly to a support member, or forming a first or second layer, is preferably detected by elemental analysis.

Figure 7:
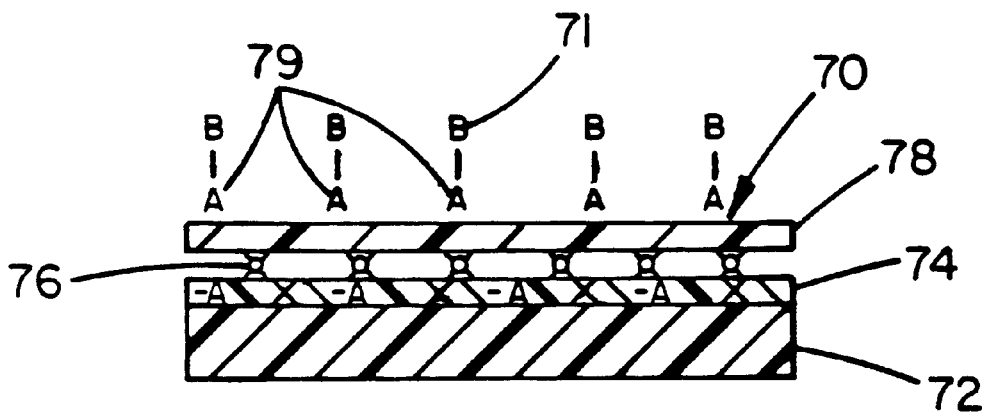
FIG. 7 illustrates a cross-section of the present invention (70) wherein a first layer (74) is attached to a support member (72) such that the number of chemically functional groups available for immobilizing bioactive species (71) from the first layer is increased by the addition of a second layer (78). The letter "x" indicates that the constituents of the first layer are cross-linked together. The symbol "¤" (76) represents excess chemically functional groups of the cross-linking agent. The symbol "-A" in the region depicting the first layer indicates chemically functional groups of the constituents of the first layer that have been consumed during the formation of the first layer and are no longer available for immobilization of bioactive species. The letter "A" on the second layer represents unreacted chemically functional groups of the constituents of the second layer that are available for immobilization of bioactive species or attachment of additional layers of hydrophilic materials thereto. The letter "B" (71) in FIG. 7 represents a bioactive species.

The composition of the second layer is chosen both for the ability of the second layer to cooperate with the first layer to promote wetting of the hydrophobic support member with high surface tension fluids and for its ability to provide a variety of chemically functional groups not usually present on the first layer to which bioactive species can be immobilized. When forming the second layer, various hydrophilic polymers may be selected for use in making the layer. Different hydrophilic polymers provide a variety of chemically functional groups to select from when attaching bioactive species to the second layer (See FIG. 7). As a result, the chemically functional groups of the second layer dictate the type and number of functional groups available for immobilization of bioactive species thereto.

Furthermore, attachment of a second layer onto the unconsumed moieties of the cross-linking agent amplifies the number of chemically functional groups available for the immobilization of bioactive species to numbers much greater than possible using only the first layer of material on the support member. This is a key feature of the present invention because the ability to select the type and the number of chemically functional groups used to immobilize bioactive species provided by the second layer is not readily obtained with the first layer alone.

Figure 1:
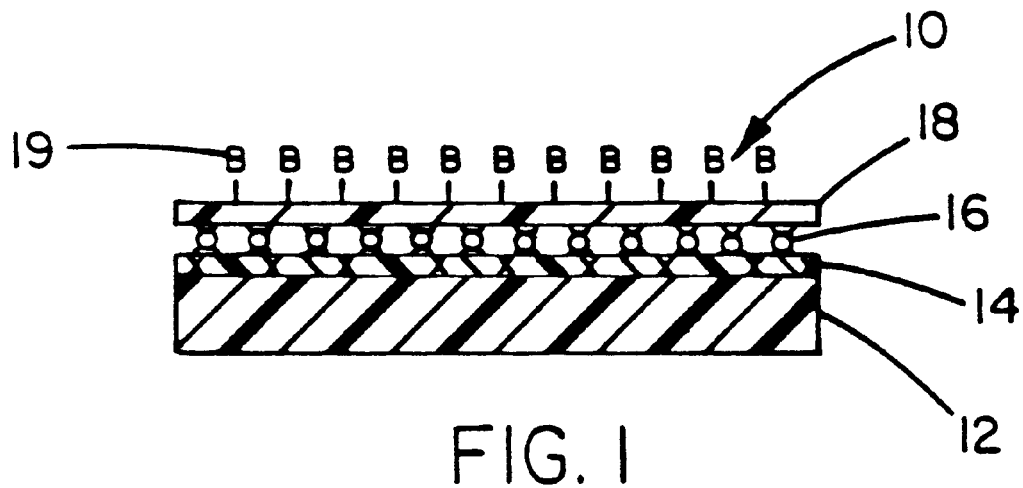
FIG. 1 illustrates a cross-section of the present invention (10) having a first layer (14) attached to a support member (12) wherein the letter "x" indicates that the constituents of the first layer are cross-linked together and the symbol "¤" (16) indicates excess chemically functional groups of the cross-linking agent to which a second layer (18) is attached. The letter "B" (19) in FIG. 1 represents a bioactive species.
Figure 2:
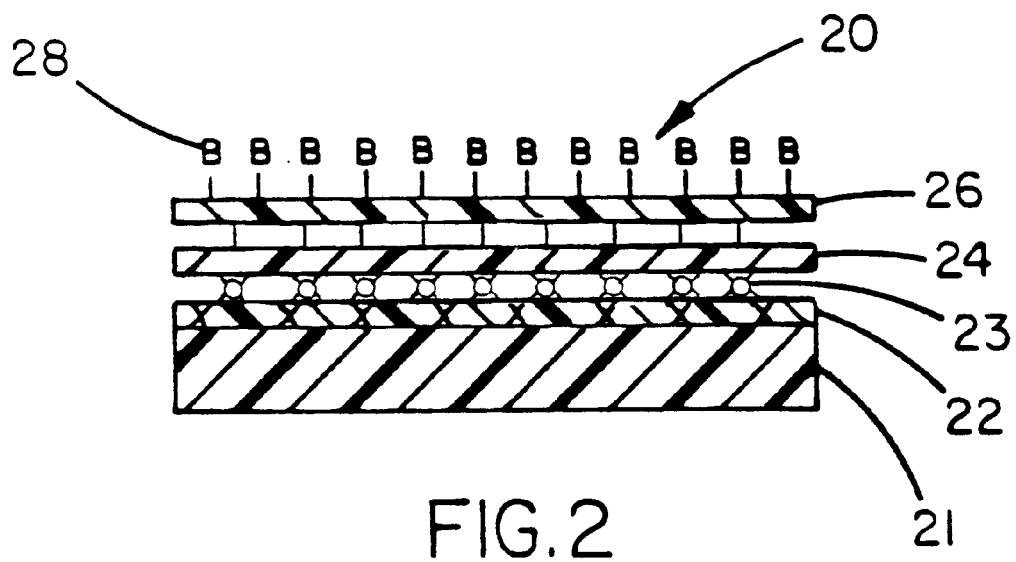
FIG. 2 illustrates a cross-section of the present invention (20) having an additional layer (26) of hydrophilic polymers attached to a second layer (24) with bioactive species (28) immobilized to the additional layer (26). The letter "x" indicates that the constituents of the first layer (22) are cross-linked together and the symbol "¤" (23) indicates excess chemically functional groups of the cross-linking agent to which a second layer (24) is attached. The additional layer of hydrophilic polymers is represented as being attached to the second layer by a plurality of vertical lines. The letter "B" (28) in FIG. 2 represents a bioactive species.
Figure 3:
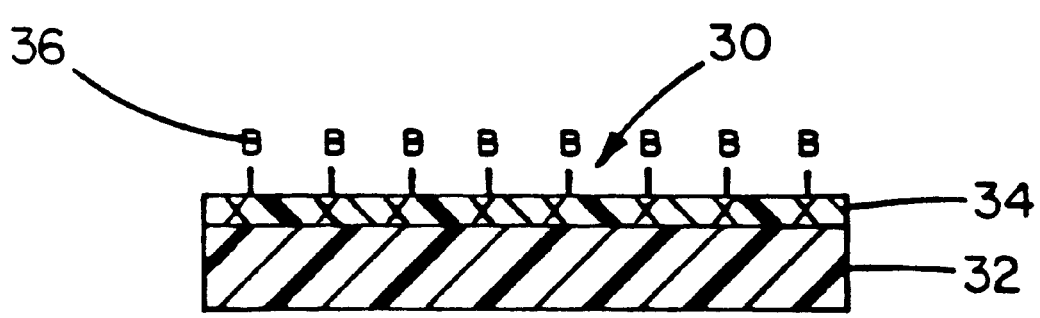
FIG. 3 illustrates a cross-section of the present invention (30) having a first layer (34) attached to a support member (32) wherein bioactive species are immobilized directly to chemically functional groups of the first layer. The letter "x" indicates that the constituents of the first layer are cross-linked together. The letter "B" in FIG. 3 represents a bioactive species (36).

A second layer is formed on the first layer by attaching a hydrophilic polymer to the cross-linked polymeric surfactant of the first layer through the unreacted chemically functional groups of the cross-linking reagent (See FIG. 1). Preferably, the hydrophilic polymers are covalently attached to the polymeric surfactants. In one method, the second layer is attached to the first layer by immersing a support member having an adsorbed and cross-linked first layer in a solution of a hydrophilic polymer of the second layer at a concentration of about 0.001% to about 99.9%, preferably about 0.1% to about 50%, more preferably about 1.0% to about 25%, and most preferably about 0.25% to about 5%. The solution of hydrophilic polymer includes an appropriate catalyst, such as organic acids or bases, mineral acids or bases, Lewis acids or bases, organometallic catalysts, organic and/or inorganic salts, heat, pressure, electron irradiation, photon irradiation, plasma irradiation, corona discharge, or pH, to effect attachment to the chemically functional groups of the first layer.

Suitable hydrophilic polymers for use in forming the second layer include, but are not limited to, polyvinyl alcohol, polylysine, poly(acrylonitrile-co-acrylic acid-acrylamidine), polyacrylic acid, polyhydroxyethylmethacrylate, polyvinylpyrrolidone, polyethylene glycol, alginate, sepharose, mercaptosilane, aminosilane, hydroxylsilane, agarose, polyethyleneimine, polyallylamine, polyaminoethylmethacrylate, polyornithine, polyaminoacrylamide, polyacrylamide, polyacrolein, polyacryloxysuccinimide, polysulfone, poly(acrylonitrile-co-acrylamide), or their copolymers, either alone or in combination. Polyvinyl alcohol is preferred. Suitable solvents for dissolving the hydrophilic polymers include, but are not limited to, water, alcohols, dioxane, dimethylformamide, tetrahydrofuran, and acetonitrile, etc.

Once a second layer is formed on the first layer, bioactive species are then immobilized onto the second layer using mild bioconjugation techniques known to those skilled in the art (See K. Mosbach, Immobilized Enzymes and Cells, Part B, Academic Press (Orlando, Fla.), (1987); G. T. Hermanson, A. K. Mallia, P. K. Smith, "Immobilized Affinity Ligand Techniques," Academic Press, San Diego, (1992); S. F. Karel, S. B. Libicki, C. R. Robertson, "The Immobilization of Whole Cells: Engineering Principles," Chemical Eng. Sci., 40: 1321 (1985); and M. Brinkley, "A Brief Survey Of Methods For Preparing Protein Conjugates With Dyes, Haptens, and Cross-linking Reagents," Bioconjugate Chem., 3:2 (1992), for example). Mild bioconjugation schemes are preferred for immobilization of bioactive species in order to eliminate or minimize damage to the structure of the support member, the polymeric surfactant of the first layer, the hydrophilic polymer of the second layer, and the bioactive species.

Figure 8:
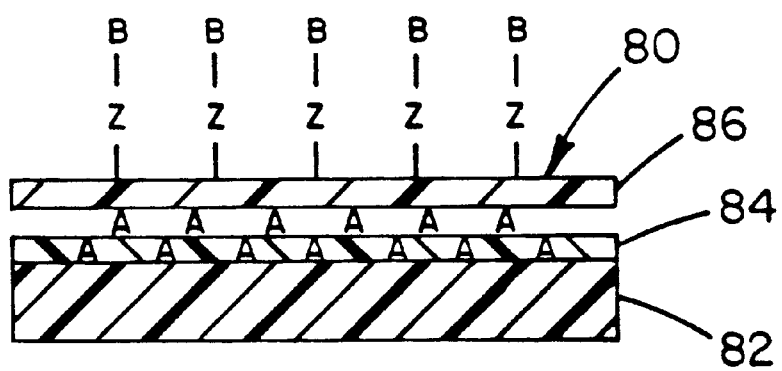
FIG. 8 illustrates a cross-section of the present invention (80) having a first layer (84) attached to a support member (82) and a second layer (86) attached to the first layer wherein a variety of chemically functional groups is provided by the second layer. The chemically functional groups of the first layer are represented by the letter "A." Chemically functional groups of the second layer may be the same as the chemically functional groups of the first layer or the groups may be different. The chemically functional groups of the second layer are represented by the letter "Z." The letter "B" in FIG. 8 represents a bioactive species.
Figure 9:
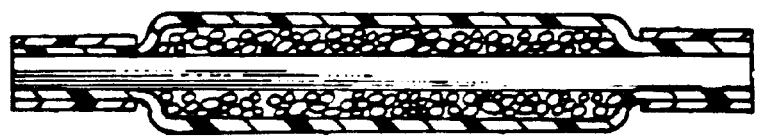
FIG. 9 illustrates a cell encapsulation device using a membrane constructed according to the present invention.

Referring to FIG. 8, the chemically functional groups of the first layer include, but are not limited to, hydroxyl groups, carboxyl groups, acid anhydride groups, acyl halide groups, alkyl halide groups, aldehyde groups, alkene groups, amide groups, amine groups, guanidine groups, malimide groups, thiol groups, sulfonate groups, sulfonyl halide groups, sulfonyl ester groups, carbodiimide groups, ester groups, cyano groups, epoxide groups, proline groups, disulfide groups, imidazole groups, imide groups, imine groups, isocyanate groups, isothiocyanate groups, nitro groups, and azide groups. The chemically functional groups of the first layer are depicted in FIG. 8 as the letter "A." The chemically functional groups of the second layer include, but are not limited to, any of the groups listed for the first layer and/or hydroxyl groups, carboxyl groups, acid anhydride groups, acyl halide groups, alkyl halide groups, aldehyde groups, alkene groups, amide groups, amine groups, guanidine groups, malimide groups, thiol groups, sulfonate groups, sulfonyl halide groups, sulfonyl ester groups, carbodiimide groups, ester groups, cyano groups, epoxide groups, proline groups, disulfide groups, imidazole groups, imide groups, imine groups, isocyanate groups, isothiocyanate groups, nitro groups, and azide groups. The chemically functional groups of the second layer are represented in FIG. 8 by the letter "Z."

In addition to providing variability in the number and identity of chemically functional groups that can be used to immobilize bioactive species, variability in the number and identity of the functional groups of the second layer can be used to increase the wettability of the support member with high surface tension fluids. In one embodiment, a porous hydrophobic support member is modified only at its surface by a thin first and second layer, leaving the material defining the porous void spaces of the support member unmodified and hydrophobic. In another embodiment, the first and second layers can also be formed on the material defining the interior porous void spaces of the porous support member and bioactive species immobilized thereon. In this embodiment, a continuous water phase through the pores of the support member can be readily established and maintained, resulting in good transport of reaction products or nutrients, for example, across the porous support member. Thin coatings are particularly preferred for porous support members because the thin coatings do not appreciably decrease the porosity of the support member. For unmodified porous PTFE having a nominal thickness of about 40 microns, a nominal pore size of about 0.2 microns, and a nominal porosity of about 70%, the material's permeability to air in Gurley seconds is between about 22 seconds to about 24 seconds. A porous PTFE material modified according to the present invention has a permeability to air of about 24 Gurley seconds to about 26 Gurley seconds.

In some circumstances, the interaction of a solution-phase reactant with an immobilized bioactive species may be suboptimal. For example, steric hinderances between the first or second layer and the immobilized bioactive species may limit the approach of the solution phase reactant to the bioactive species. In addition, physical bulk, electrostatic repulsion, or inappropriate positioning of the bioactive species may also contribute to reduced efficiency of the immobilized bioactive species. Accordingly, it may be desirable to place one or more additional compounds as a "spacer" or "tether" between the chemically functional groups of the first or second layer and the bioactive species to increase the space between the layer and the bioactive species. Suitable compounds for use as a spacer include, but are not limited to, succinic acid, diaminohexane, glyoxylic acid, short chain polyethylene glycol, and glycine, for example. It is understood that the second layer may itself serve as a spacer arm without necessitating the use of a separate spacer compound.

The covalent immobilization of biospecies onto support members according to the present invention is generally non-reversible, i.e., the biospecies is not readily released from the first or second layer of the support member. Spacers, or tethers, capable of selectively releasing an immobilized biospecies have utility in receptor/ligand interactions, molecular identification and characterization of antibody/antigen complexes, and selective purification of cell subpopulations, etc. In addition, a selectively cleavable spacer affords predictable and controlled release of biospecies from the support member as opposed to the unstable physisorption of biospecies discussed in the Background section above.

Selective release of the biospecies is performed by cleaving the spacer compound under appropriate reaction conditions including, but not limited to, photon irradiation, enzymatic degradation, oxidation/reduction, or hydrolysis, for example. The selective cleavage and release of immobilized biospecies may be accomplished using techniques known to those skilled in the art (see for example, H. R. Horton & H. E. Swaisgood, "Covalent immobilization of proteins by techniques which permit subsequent release," Meth. Enzymology, 135: 130 (1987); S. S. Wong, Chemistry of Protein Conjugation and Cross-Linking, CRC Press (1991); and U.S. Pat. No. 4,745,160, issued to Churchill et al., which is incorporated herein by reference). Suitable compounds for use as cleavable tethers, or cleavable spacers, include, but are not limited to, polyhydroxyacids, polyanhydrides, polyamino acids, tartarates, and cysteine-linkers such as Lomant's Reagent, for example.

The present invention is not limited to the above-described embodiments having a first layer and a second layer. In other embodiments, additional layers of hydrophilic polymers may be attached to existing layers on the support member to form constructions with multiple layers of hydrophilic material attached thereto.

Without intending to limit the scope of the present invention, the following examples illustrate how the present invention can be made and used.

EXAMPLES

Example 1

This example illustrates a method for forming a first layer comprised of polymeric surfactants on an expanded polytetrafluoroethylene support member by adsorption and cross-linking of the polymeric surfactant on the exterior surfaces of an expanded polytetrafluoroethylene film, as well as, the surfaces delineating the porous regions of the film. The method is as follows.

An ePTFE support member in the form of a film (W. L. Gore & Associates, Inc.), having a thickness of about 50 μm and a porosity as measured in Gurley seconds of about 22 to 24, was immersed in a 1.5% solution of a random copolymer of tetrafluoroethylene and vinyl alcohol (hereinafter HPL-1, Japan GORE-TEX, Inc.) in methanol (w/v) for about 5 minutes. This film construction was then immersed in methanol for about 5 minutes to rinse unadsorbed bulk copolymer from the ePTFE surface. The ePTFE support member with the HPL-1 layer was then washed free of methanol by immersing in distilled water for about 5 minutes.

The adsorbed layer of HPL-1 was cross-linked in situ on the ePTFE support member by dipping the film construction in an aqueous solution of about 5% glutaraldehyde, with about 1% HCl as catalyst, for about 5 minutes, at about 70° C. to cross-link the vinyl alcohol groups of the adsorbed HPL-1 copolymer chains via acetalization. This film construction was rinsed in water to remove excess glutaraldehyde and HCl. The resulting film construction was an ePTFE support member having a first layer formed thereon.

Example 2

This example illustrates the stability of the first layer of the film construction described in Example 1. The stability of a particular layer is expressed in terms of the hydrophilicity of the surface of the film construction. As mentioned above, a hydrophilic surface is a surface that is readily wetted with high surface tension fluids. To compare the hydrophilicity of one surface with another surface, a drop of water is placed on the test surface and its behavior observed. If the water drop spread on the surface of the material to wet and fill the pores of the material with water and render the material transparent, the surface of the material was considered to be hydrophilic. If the water drop did not spread on the surface of the material or wet the pores to fill them substantially completely with water, but rounded up on the surface of the material, rendering the material translucent or opaque, the surface of the material was considered to be hydrophobic.

To test the stability of the first layer of the film construction, two film constructions were used. A first film construction was made as described in Example 1. A second film construction was made similarly to the film construction of Example 1, but without the cross-linking step. Both constructions were immersed in various refluxing solvents, such as water, dimethyl formamide (DMF), dimethyl sulfoxide (DMSO), and acetone, for about 24 hours. The film constructions were then removed from the solvent, rinsed in fresh solvent, and air dried. The hydrophilicity of the particular surface was then tested by applying one or more drops of deionized water to the surface. The second film construction showed a significant decrease in the hydrophilicity of the surfaces of the construction. The reduced hydrophilicity was believed to be due primarily to desorption of the copolymer from the surface of the constructions and to copolymer chain migration on the surface of the constructions. The film construction of Example 1, i.e., with cross-linking, remained hydrophilic under the same conditions.

In another stability test, first and second film constructions were steam autoclaved ten times at about 120° C. for about 15 minutes each, air dried, and then dipped in deionized water. When the second film construction was dipped in deionized water, the construction was considered hydrophobic. In contrast, the first film construction became spontaneously wetted to completion with the deionized water and so was considered hydrophilic. These results are believed to indicate surface instability and clustering on the surface the second film construction, leading to a reduction of wetting potential. On the other hand, the first film construction, in which the first layer was cross-linked, showed surfactant stability.

Example 3

This example illustrates use of another reagent for cross-linking the polymeric surfactant of Example 1. The method is as follows.

Following adsorption of the surfactant to the surfaces of the ePTFE support member in Example 1, the film construction was dipped in an aqueous solution of about 2% polyethylene glycol dialdehyde (3400 g/mol, Shearwater Polymers), with about 0.1% HCl as catalyst, for about 30 minutes, at about 75° C., to cross-link the vinyl alcohol groups of the adsorbed HPL-1 copolymer chains via acetalization. This film construction was rinsed in water to remove excess polyethylene glycol dialdehyde and HCl. The resulting film construction was an ePTFE support member having a first layer formed thereon.

Example 4

This example illustrates use of another reagent for cross-linking the polymeric surfactant of Example 1. The method is adapted from U.S. Pat. No. 5,354,587, issued to Abaysekara, and is performed as follows.

Following adsorption of the surfactant to the surfaces of the ePTFE support member in Example 1, the film construction was dipped in a methanolic solution of about 0.25% potassium hydroxide (KOH) for about 30 seconds followed by air drying. The film construction was then dipped in an acetone solution of about 10% polyethylene glycol diglycidyl ether (400 g/mol, Polysciences) for about 5 minutes. The film construction was cured in vacuo at about 75° C. for about 3 hours to cross-link the vinyl alcohol groups of the adsorbed HPL-1 copolymer chains via epoxide alcoholysis. The film construction was rinsed in distilled water to remove excess polyethylene glycol diglycidyl ether and KOH. The resulting film construction was an ePTFE support member having a first layer formed thereon.

Example 5

This example illustrates the stability of the first layer of the film construction described in Example 4. The stability of a particular layer is expressed in terms of the hydrophilicity of the surface of the film construction. As mentioned above, a hydrophilic surface is a surface that is readily wetted with high surface tension fluids. To compare the hydrophilicity of one surface with another surface, a drop of water is placed on the test surface and its behavior observed. If the water drop spread on the surface of the material to wet and fill the pores of the material with water and render the material transparent, the surface of the material was considered to be hydrophilic. If the water drop did not spread on the surface of the material or wet the pores to fill them substantially completely with water, but rounded up on the surface and rendered the material translucent or opaque, the surface of the material was considered to be hydrophobic.

To test the stability of the first layer of the film construction, two film constructions were used. A first film construction was made as described in Example 4. A second film construction was made similarly to the film construction of Example 4, but without the crosslinking step. Both constructions were immersed in various refluxing solvents, such as water, dimethyl formamide (DMF) for about 24 hours. The film constructions were then removed from the solvent, rinsed in fresh solvent, and air dried. The hydrophilicity of the particular surface was then tested by applying one or more drops of deionized water to the surface. The second film construction showed a significant decrease in the hydrophilicity of the surfaces of the film construction. The reduced hydrophilicity was believed to be due primarily to desorption of the copolymer from the surface of the constructions and to copolymer chain migration on the surface of the constructions. The first film construction, i.e., with cross-linking, remained hydrophilic under the same conditions.

In another stability test, the first and second film constructions were steam autoclaved at about 120° C. for about 20 minutes, air dried, and then dipped in deionized water. When the second film construction was dipped in deionized water, the film construction was considered hydrophobic. In contrast, the first film construction became spontaneously wetted to completion with the deionized water and so was considered hydrophilic. These results are believed to indicate surface instability and clustering on the surface of the second film construction, leading to a reduction of wetting potential. On the other hand, the first film construction showed surfactant stability.

Example 6

This example illustrates a method for forming a first layer comprised of polymeric surfactants on an expanded polytetrafluoroethylene support member by adsorption and cross-linking of the polymeric surfactant on the exterior surfaces of an expanded polytetrafluoroethylene film, as well as, the surfaces delineating the porous regions of the film. The method is as follows.

An ePTFE support member in the form of a film (W. L. Gore & Associates, Inc.), having a thickness of about 50 μm and a porosity as measured in Gurley seconds of about 22 to 24, was prewetted with isopropyl alcohol and then immersed in a solution of about 1% polyvinyl alcohol (PVA) (Sigma) in distilled water (w/v) for about 5 minutes. This film construction was then immersed in distilled water for about 10 minutes to rinse unadsorbed bulk copolymer from the ePTFE surface.

The adsorbed layer of PVA was cross-linked in situ on the ePTFE support member by dipping the film construction in an aqueous solution of about 5% glutaraldehyde, with about 1% HCl as catalyst, for about 20 minutes, at about 25° C. to cross-link the vinyl alcohol groups of the adsorbed PVA copolymer chains via acetalization. This film construction was rinsed in water to remove excess glutaraldehyde and HCl. The resulting film construction was an ePTFE support member having a first layer formed thereon.

Example 7

This example illustrates used of another reagent for cross-linking the polymeric surfactants of Example 6. The method is as follows.

Following adsorption of the surfactant to the surfaces of the ePTFE support member in Example 6, the film construction was dipped in an aqueous solution of about 2% polyethylene glycol dialdehyde (3400 g/mol, Shearwater Polymers), with about 0.1% HCl as catalyst, for about 30 minutes, at about 75° C., to cross-link the vinyl alcohol groups of the adsorbed PVA copolymer chains via acetalization. This film construction was rinsed in water to remove excess polyethylene glycol dialdehyde and HCl. The resulting film construction was an ePTFE support member having a first layer formed thereon.

Example 8

This example illustrates used of another reagent for cross-linking the polymeric surfactants of Example 6. The method is adapted from U.S. Pat. No. 5,354,587, issued to Abaysekara, and is performed as follows.

Following adsorption of the surfactant to the surfaces of the ePTFE support member in Example 6, the film construction was dipped in a methanolic solution of about 0.25% potassium hydroxide (KOH) for about 30 seconds followed by air drying. The film construction was then dipped in an acetone solution of about 10% polyethylene glycol diglycidyl ether (400 g/mol, Polysciences) for about 5 minutes. The film construction was cured in vacuo at about 75° C. for about 3 hours to cross-link the vinyl alcohol groups of the adsorbed PVA copolymer chains via epoxide alcoholysis. The film construction was rinsed in distilled water to remove excess polyethylene glycol diglycidyl ether and KOH. The resulting film construction was an ePTFE support member having a first layer formed thereon.

Example 9

This example illustrates the formation and attachment of a second layer comprised of the hydrophilic polymer polyvinyl alcohol (PVA) on the first layer formed on the ePTFE support member described in Example 1.

The film construction of Example 1 was immersed in an aqueous solution of about 1.0% polyvinyl alcohol (PVA) (Sigma), with about 1% HCl as catalyst, at about 75° C., for about 5 minutes, to allow covalent attachment of PVA to free aldehyde groups remaining after the first layer has been cross-linked. Following attachment of the second layer to the first layer via acetal linkages, excess PVA was rinsed from the film construction by immersing the construction in water. The resulting film construction was immediately and spontaneously wettable with liquid water.

Example 10

This example illustrates the formation and attachment of a second layer comprised of the hydrophilic polymer polyvinyl alcohol (PVA) on the first layer formed on the ePTFE support member described in Example 6.

The film construction of Example 6 was immersed in an aqueous solution of about 1.0% polyvinyl alcohol (PVA) (Sigma), with about 1% HCl as catalyst, at about 25° C., for about 10 minutes, to allow covalent attachment of PVA to free aldehyde groups remaining after the first layer has been cross-linked. Following attachment of the second layer to the first layer via acetal linkages, excess PVA was rinsed from the film construction by immersing the construction in water. The resulting film construction was immediately and spontaneously wettable with liquid water.

Example 11

This example illustrates the formation and attachment of a second layer comprised of the hydrophilic polymer polylysine on the first layer formed on the ePTFE support member described in Example 1.

The film construction of Example 1 was immersed in a buffered aqueous solution of about 0.5% polylysine hydrobromide (100,000 g/mol, Sigma) at about pH 9 at about 25° C. for about 2 hours to allow covalent attachment of polylysine to free surface aldehyde groups generated during cross-linking of the first layer. Cyanoborohydride was added to reduce the imine linkage to a secondary amine. Following attachment of the second layer to the first layer via imine linkages, excess polylysine was washed by immersing the film construction in distilled water. The resulting film construction was immediately and spontaneously water wettable.

Example 12

This example illustrates the formation and attachment of a second layer comprised of the hydrophilic polymer polylysine on the first layer formed on the ePTFE support member described in Example 6.

The film construction of Example 6 was immersed in a buffered aqueous solution of about 0.5% polylysine hydrobromide (100,000 g/mol, Sigma) at about pH 9 at about 25° C. for about 2 hours to allow covalent attachment of polylysine to free surface aldehyde groups generated during cross-linking of the first layer. Following attachment of the second layer to the first layer via imine linkages, excess polylysine was washed by immersing the film construction in distilled water. Cyanoborohydride was added to reduce the imine linkage to a secondary amine. The resulting film construction was immediately and spontaneously water wettable.

Example 13

This example illustrates the stability of the first and second layers of the film construction described in Example 9. In the stability test, the film construction of Example 9 was extracted in dimethyl formamide (DMF) at about 120° C. for about 2 days. No statistically significant decrease in the mass of the construction was observed using gravimetry, indicating no detectable desorption of the first and second layers from the surface of the support member. This film construction spontaneously and completely wetted with liquid water. As a result, the surface of the film construction was considered to be stably hydrophilic.

In another stability test of the first and second layers of the film construction of Example 9, the film construction was immersed in about 5% HCl at about 80° C. for about 2 days, rinsed in water, and then air dried. Following this treatment, the film construction remained hydrophilic.

Example 14

This example illustrates the stability of the first and second layers of the film construction described in Example 10. In the stability test, the film construction of Example 10 was extracted in dimethyl formamide (DMF) at about 120° C. for about 1 day. No statistically significant decrease in the mass of the construction was observed using gravimetry, indicating no detectable desorption of the first and second layers from the surface of the support member. This film construction spontaneously and completely wetted with liquid water. As a result, the surface of the film construction was considered to be stably hydrophilic.

In another stability test of the first and second layers of the film construction of Example 10, the film construction was immersed in about 5% HCl at about 80° C. for about 2 days, rinsed in water, and then air dried. Following this treatment, the film construction remained hydrophilic.

Example 15

This example illustrates the stability of the first and second layers of the film construction described in Example 9. In the stability test, the film construction of Example 9 was extracted in distilled water at about 25° C. for about 7 days. No statistically significant decrease in the mass of the construction was observed using gravimetry, indicating no detectable desorption of the first and second layers from the surface of the support member. This film construction spontaneously and completely wetted with liquid water. As a result, the surface of the film construction was considered to be stably hydrophilic.

Example 16

This example illustrates the stability of the first and second layers of the film construction described in Example 10. In the stability test, the film construction of Example 10 was extracted in distilled water at about 25° C. for about 7 days. No statistically significant decrease in the mass of the construction was observed using gravimetry, indicating no detectable desorption of the first and second layers from the surface of the support member. This film construction spontaneously and completely wetted with liquid water. As a result, the surface of the film construction was considered to be stably hydrophilic.

Example 17

This example illustrates the lack of decreased permeability of a film construction as described in Example 9. To evaluate the permeability of the film construction, scanning electron micrographs were first taken of the microstructure of the film construction to view the first and second layers on the nodes and fibrils of the ePTFE support member. The results of these micrographs showed no visible plugging of pores or bulk deposition of surfactant therein (See FIG. 5). This indicates that the adsorption and cross-linking of the first layer and attachment of the second layer was very thin.

To further demonstrate that surfactant-treated ePTFE does not increase resistance to mass transport by plugging of pores, pore size was measured using a Coulter Porometer. A film construction was prepared as described in Example 9 and helically wrapped around a cylindrical mandrel to form a tube. The mean pore size of the film-tube construction was measured to be 0.173±0.006 $\mu$m, while the mean pore size of a similar untreated ePTFE tubing was measured to be 0.180±0.001 $\mu$m. These data indicate no statistically significant blockage of pores due to the first and second layers.

To further demonstrate that an ePTFE support member having a first and second layer of the present invention does not increase resistance to mass transport by plugging of pores, the permeability of the film construction to glucose flux was measured. To test the permeability of the film construction to glucose flux an ePTFE film-tube construction was prepared as previously described. The glucose mass transport coefficient of the film-tube construction was measured to be 0.98 $\mu$m/sec, while the glucose mass transport coefficient of a similar untreated ePTFE tubing was measured to be 0.25 $\mu$m/sec. These data indicate that the diffusion of glucose across the film-tube construction of the present invention was greater than for the untreated material due to the presence of a more continuous water phase in the pores that traversed the thickness of the support member.

Example 18

This example illustrates the immobilization of a bioactive species in the form of peptides to a film construction of the present invention as described in Example 10. To begin the process, the film construction of Example 10 was immersed in an acetone solution containing about 5% carbonyidiimidazole (Sigma) for about 60 minutes to convert vinyl alcohol groups to reactive imidazole carbamates. The film construction was rinsed in acetone, then immersed in a buffered solution of about 0.1% Gly-Arg-Gly-Asp-Ser (Sigma) at about pH 9 for about 24 hours at about 4° C. to allow conjugation of the peptide onto the imidazole carbamates. Excess imidazole groups were converted back to vinyl alcohol groups via hydrolysis in water at about pH 7.4 for about 24 hours.

Example 19

This example also illustrates the immobilization of a bioactive species in the form of peptides to a film construction of the present invention as described in Example 9. To begin the process, the film construction of Example 9 was immersed in a dimethylformamide (DMF) solution containing about 10% hexamethylene diisocyanate (Aldrich), with about 0.5% dimethylaminopyridine as catalyst, for about 1 hour in order to place free isocyanate groups upon the PVA layer ( protocol adapted from A. Kondoh, K. Makino, T. Matsuda, "Two-Dimensional Artificial Extracellular Matrix: Bioadhesive Peptide-Immobilized Surface Design," J. Applied Polym. Sci., 47: 1983 (1993)). The film construction was then rinsed in aqueous 1M KOH to hydrolyze the free isocyanates to free amines, after which it was immersed in a DMF solution containing about 0.5% disuccinimidyl suberate (Pierce) for about 1 hour to place free succinimidyl groups upon the free amines. The film construction was rinsed in DMF, then immersed in a buffered solution of about 0.1% Gly-Arg-Gly-Asp-Ser (Sigma) at about pH 9 for about 12 hours to allow conjugation of the peptide onto the free succinimidyl groups.

Example 20

This example also illustrates the immobilization of a bioactive species in the form of peptides to a film construction of the present invention as described in Example 9. To begin the process, the film construction of Example 9 was immersed in a solution of about 5% glyoxylic acid (Sigma), with 1% HCl as catalyst, for about 15 minutes at about 80° C. to acetalize the PVA of the second layer, thereby conjugating free carboxylic acid groups. The film construction was then immersed in an acetone solution of about 1% N,N,N',N'-tetramethyl-O-(N-succinimidyl)uronium tetrafluoroborate (Fluka), with about 0.25% dimethylaminopyridine as catalyst, for about 2 hours, to convert the carboxylic acids to reactive succinimidyl esters. The film construction was rinsed in acetone, then immersed in a buffered solution of about 0.1% Gly-Arg-Gly-Asp-Ser (Sigma) at about pH 9 for about 24 hours to allow conjugation of the peptide onto the succinimidyl groups.

Example 21

This example also illustrates the immobilization of a bioactive species in the form of peptides to a film construction of the present invention as described in Example 9. To begin the process, the film construction of Example 9 is immersed in a solution of about 5% glyoxylic acid, with about 1% HCl as catalyst, for about 10 minutes at about 80° C. to place free carboxylic acid groups upon the PVA layer. The film construction is immersed in an aqueous buffered solution of about 1% 1-ethyl-3-(dimethylaminopropyl) carbodiimide (EDC) (Sigma) at about pH 5 for about 1 hour at about 4° C. to convert the carboxylic acids to reactive O-acylureas. The film construction is rinsed in the buffered solution, then immersed in the buffered solution with about 0.1% Gly-Arg-Gly-Asp-Ser (Sigma) at about pH 9 for about 24 hours to allow conjugation of the peptide onto the O-acylureas.

Example 22

This example illustrates the immobilization of a bioactive species in the form of cells to a film construction of the present invention as described in Example 18. To begin the process, the film construction of Example 18 was seeded with rat insulinoma cells in cell culture medium. These cells have receptors that assist the cells in adhering to certain substrates or ligands. The ligand, Gly-Arg-Gly-Asp-Ser, described in Example 18 is commonly known to bind to receptors on cells involved in adhesion of the cell to other cells, or other substrates. In the present invention, the Arg-Gly-Asp ligand was used to immobilize the rat insulinoma cells to the film construction of Example 18. As a comparison, unmodified ePTFE, ePTFE modified with a polyvinyl alcohol surfactant according to Example 10, but without Gly-Arg-Gly-Asp-Ser, and tissue culture polystyrene were each seeded with the same cells. Due to inertness, hydrophobicity, and slippery texture of ePTFE, cells do not easily adhere to ePTFE, if at all. Tissue culture polystyrene is commonly used as a substrate for a wide variety of cells in tissue culture. The extent of cell adhesion was quantified by visualizing the cells under phase contrast microscopy 12 hours after the cell seeding.

The results of these tests showed that tissue culture polystyrene supported spreading of all seeded cells after 12 hours, as expected. Similar results were seen with the film construction of Example 18. Unmodified ePTFE and PVA-modified ePTFE made according to Example 10 supported less than 5% spread cells at 12 hours, however. These data indicate, among other things, that the immobilization of cells onto ePTFE was enhanced by immobilizing bioactive ligands for which the cells have receptors onto the ePTFE surface. The data also indicate that the presence of a first and second layer alone did not improve cell immobilization.

Example 23

A cell encapsulation device of the type disclosed by Butler et al. in co-pending U.S. patent application Ser. No. 08/532,925, filed Sep. 22, 1995, entitled "Improved Cell Encapsulation Device," which is incorporated herein by reference, was made using the film construction of Example 10 as the cell encapsulation membrane, or cover, of the device. In preferred embodiments of the Butler et al. device, the geometry is essentially cylindrical. An important feature of the device is a cell displacing core located in the center of the device to place cells away form the center of the device near the cell encapsulation membrane where maximum exchange of nutrients, gases, wastes, and cell products between cells encapsulated in the device and the external environment of the device can occur.

A film construction as described in Example 10 was made and helically wrapped on a cylindrical mandrel to form a tube, or cover, about 3 cm in length, having an inner diameter of about 1.7 cm. A hydrogel rod, or core, about 3 cm in length, having an outer diameter of about 1.6 cm was inserted into the tube. The tube was sealed at one end by applying a constrictive silicone rubber cuff over the tube and the core (See FIG. 8). Using a syringe, the device was filled with a slurry of adhesion-independent rat insulinoma cells in cell culture medium. The remaining open end of the tube was sealed using a constrictive silicone rubber cuffs to prevent passage of cells out of the tube.

As the cells were being loaded into the device, the first and second layers of the film construction of the tube caused the tube to spontaneously wet when exposed to the culture medium. As the tube became wetted with the aqueous portion of the culture medium, the tube became transparent, allowing visualization of the cells contained therein. The cell encapsulation device was maintained in vitro using standard cell culture techniques. The viability of the cells was assessed by monitoring glucose metabolism. The cells remained viable and produced lactic acid via glycolysis while enclosed in the device for up to 3 weeks. These results demonstrate the presence of a continuous water phase across the film construction of the present invention sufficient for diffusion of nutrients, gasses, and wastes for cells to remain viable. The results also demonstrate that the film construction of the present invention was not toxic to cells.

Example 24

Many mammalian cells useful for biotechnology are adhesion dependent. For proper health of these cells, the cells must have a suitable surface upon which to adhere and spread. If the cells are not provided with a suitable surface, their metabolic output may be reduced, and in extreme circumstances cell death may occur. The present example illustrates that a membrane as described in Example 18 and formed into an assembly according to Example 23 may also maintain the viability of adhesion-dependent smooth muscle cells.

Two film-tube constructions were initially made. A first construction was made as described in Example 18 having the peptide ligand Gly-Arg-Gly-Asp-Ser. A second construction similar to Example 10 was made. Each film construction was formed into a cell encapsulation device according to Example 23, following autoclaving. A hydrogel core in the form of a rod was inserted into each tubular cell encapsulation device. One end of each device was sealed with a constrictive silicone rubber cuff as described in Example 23. Each device was filled with a slurry of canine smooth muscle cells in cell culture medium. The remaining open end of each device was sealed using constrictive silicone rubber cuffs to prevent passage of cells out of the device. The film-tube construction of both cell encapsulation devices spontaneously wetted when exposed to the culture medium. The wetted film-tube constructions became transparent and allowed visualization of the cells contained within the device. Both cell encapsulation devices were maintained in vitro using standard cell culture techniques.

The morphological state of the cells was assessed by phase contrast microscopy. Cells immobilized within the second film construction were unspread on the surface of the construction with much cellular debris observed after 4 days in culture. Cells immobilized within the first film construction were spread upon the surface of the film-tube construction. The cells remained spread on the surface of the first film construction for up to 16 weeks. These data suggest that for the immobilization of certain cell types, the presence of a continuous water phase for the transport of nutrients may be inadequate for their morphology and immobilization. Surface-bound bioactive ligands may be necessary for the proper morphology and viability of immobilized adhesion-dependent cell types.

Example 25

In the present invention, spacer arms may be provided as a tether, or linkage, to provide a physical space between the bioactive species and the second layer in order to relieve steric limitations between these two components. A variety of hydrophilic and hydrophobic spacer arms may be attached onto the multilayered structure using techniques known to those skilled in the art. For example, the film construction of Example 9 was immersed in an aqueous solution of about 5%-polyethylene glycol dialdehyde (3400 g/mol, Shearwater Polymers), with 1% HCl as catalyst, for about 5 minutes, at about 80° C., to place free aldehyde groups on the PVA surface tethered by a PEG chain. Bioactive species were then be immobilized onto these free aldehydes using techniques known to those skilled in the art.

Example 26

Using the protocol of Example 18, a Gly-Arg-Gly-Asp-Ser ligand was immobilized to the luminal surface of an ePTFE vascular graft (W. L. Gore & Associates, Inc., Flagstaff, Ariz.). Following autoclaving, the graft was seeded with canine endothelial cells. The cells were allowed to adhere for 10 days in culture. Adhesion of the endothelial cells was assessed using a stain specific for endothelial low density lipoprotein (LDL) vacuoles (Biomedical Technologies). The LDL stain showed a confluent monolayer of functional endothelial cells covering the entire treated surface of the vascular graft.

Example 27

A vascular graft having a 6 mm inner diameter made according to Example 26 was grafted in a greyhound dog as a femoral-popliteal artery by-pass for 2 hours. No anticoagulants were used in the experiment. At the end of the 2 hour period, the graft was removed and examined for the presence of endothelial cells immobilized on the luminal surface of the graft. Endothelial cells were observed on the luminal surface of the vascular graft following the 2 hour test. Little or no thrombus formation was observed on the luminal surface of the graft.

Example 28

As demonstrated in Example 22, adhesion-dependent cell types may require the presence of a surface bound peptide factor for immobilization. Cells were not immobilized onto the untreated hydrophobic ePTFE support member, but were attached to the two layer PVA system having the bioactive species Gly-Arg-Gly-Asp-Ser immobilized thereon as per Example 22. Therefore, cells may be immobilized onto a support member in a pattern by placing the first layer, the second layer, and the bioactive species in specific locations on the support member.

Figure 10:
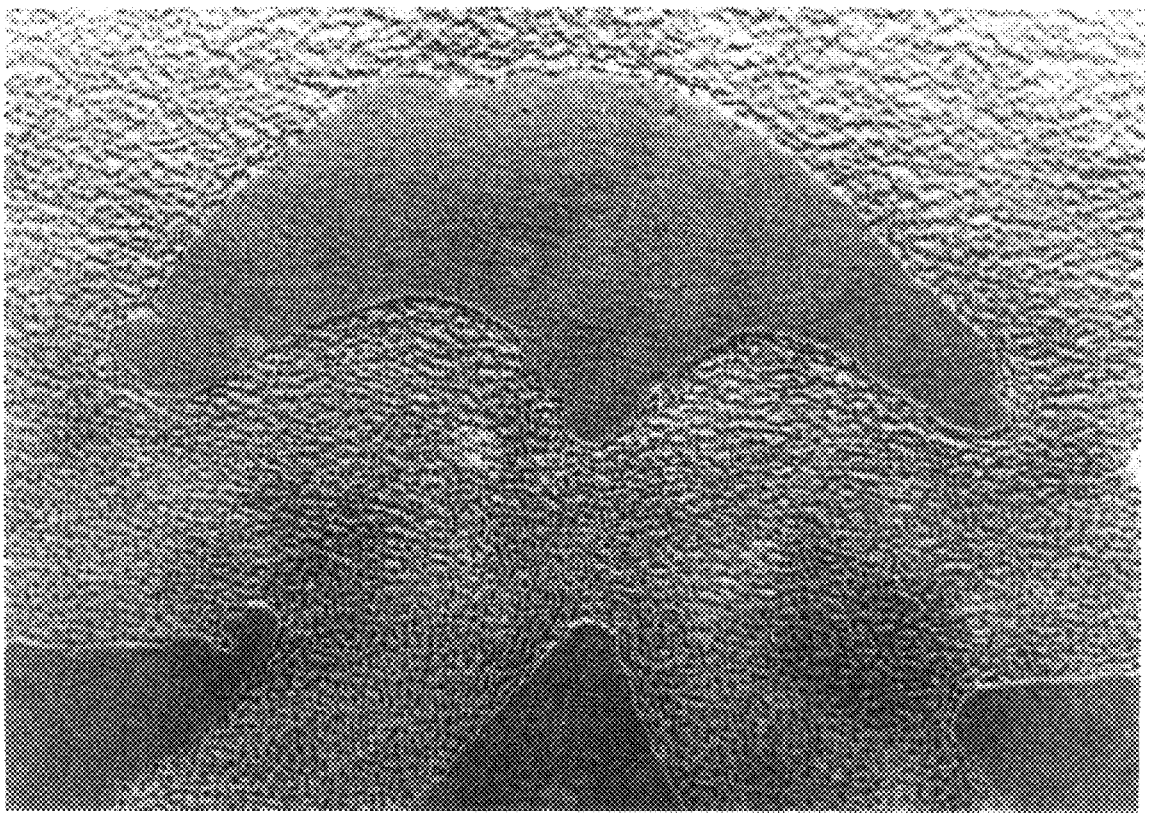
FIG. 10 is a photograph of an embodiment of the present invention wherein a bioactive species is immobilized in a pattern on porous polytetrafluoroethylene.
Figure 11:
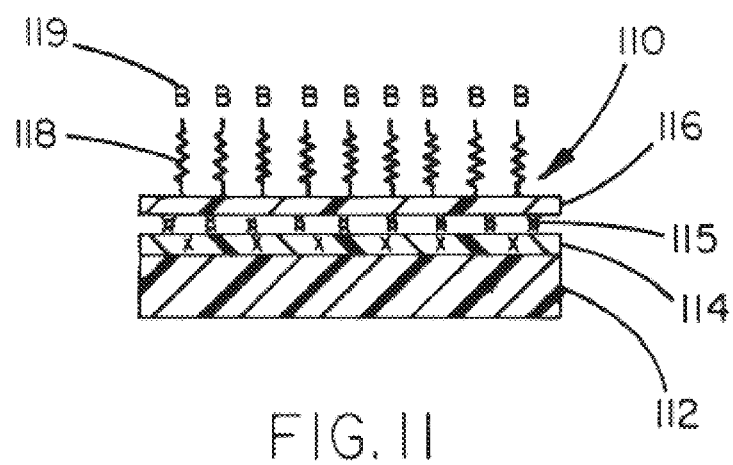
FIG. 11 illustrates a cross-section of the present invention (110) having a first layer (114) attached to a support member (112) and a second layer (116) attached to the first layer wherein a spacer compound (118) is interposed between the second layer and a bioactive species. The letter "x" indicates that the constituents of the first layer are cross-linked together. The symbol "¤" (115) represents excess chemically functional groups of the cross-linking agent. The letter "B" (119) in FIG. 11 represents a bioactive species.

For example, a construction of Example 10 was sandwiched between two other identical membranes. A rubber stamp having a distinct pattern was wetted with isopropyl alcohol. The isopropyl alcohol was applied to the membrane "sandwich" to wet all the ePTFE layers with only the pattern of the stamp. The membrane sandwich was then treated according to the protocol of Example 18 to conjugate the peptide in the shape of the pattern on the rubber stamp. The central membrane was removed from the sandwich configuration and seeded with canine endothelial cells. After about 12 hours, cells were immobilized in the shape of the pattern. No cells were seen adhered to the area of the ePTFE support member where the conjugated peptide had not been immobilized. The immobilized canine cells remained viable, immobilized, and confined to the patterned area of the support member for at least 4 weeks. See FIG. 10, for example.

Example 29

This example illustrates the present invention having a support member comprised of a polyester material. A film of polyester (Poretics) is first immersed in isopropanol to wet the membrane. The film is then immersed in a solution of 1% polyvinyl alcohol (PVA) (Sigma) for about 5 min to allow adsorption of the PVA. Next, the film is rinsed in deionized water for about 10 min. Lastly, the film is immersed in a solution of about 5% glutaraldehyde and about 1% HCl for about 20 minutes to cross-link the PVA in situ. The resulting film construction is expected to be a polyester support member having a first layer formed thereon.

Example 30

This example illustrates the present invention having a support member comprised of a polycarbonate material. A film of polycarbonate (Poretics) is first immersed in isopropanol to wet the membrane. The film is then immersed in a solution of 1% polyvinyl alcohol (PVA) (Sigma) for about 5 min to allow adsorption of the PVA. Next, the film is rinsed in deionized water for about 10 min. Lastly, the film is immersed in a solution of about 5% glutaraldehyde and about 1% HCl for about 20 minutes to cross-link the PVA in situ. The resulting film construction is expected to be a polycarbonate support member having a first layer formed thereon.

Example 31

This example illustrates the present invention having a support member comprised of a polyethylene material. A film of polypropylene (Whatman) is first immersed in isopropanol to wet the membrane. The film is then immersed in a solution of 1% polyvinyl alcohol (PVA) (Sigma) for about 5 min to allow adsorption of the PVA. Next, the film is rinsed in deionized water for about 10 min. Lastly, the film is immersed in a solution of about 5% glutaraldehyde and about 1% HCl for about 20 minutes to cross-link the PVA in situ. The resulting film construction is expected to be a polyethylene support member having a first layer formed thereon.

Example 32

This example illustrates the present invention having a support member comprised of a polyvinylidenefluoride material. A film of polyvinylidenefluoride (Millipore) is first immersed in isopropanol to wet the membrane. The film is then immersed in a solution of 1% polyvinyl alcohol (PVA) (Sigma) for about 5 min to allow adsorption of the PVA. Next, the film is rinsed in deionized water for about 10 min. Lastly, the film is immersed in a solution of about 5% glutaraldehyde and about 1% HCl for about 20 minutes to cross-link the PVA in situ. The resulting film construction is expected to be a polyvinylidenefluoride support member having a first layer formed thereon.

Example 33

This example illustrates the present invention having a support member comprised of silver metal. A membrane of silver metal (Poretics) is first immersed in isopropanol to wet the metal. The metal is then immersed in a solution of 1% polyvinyl alcohol (PVA) (Sigma) for about 5 min to allow adsorption of the PVA. Next, the metal is rinsed in deionized water for about 10 min. Lastly, the metal is immersed in a solution of about 5% glutaraldehyde and about 1% HCl for about 20 minutes to cross-link the PVA in situ. The resulting film construction is expected to be a silver metal support member having a first layer formed thereon.

Example 34

This example illustrates the present invention having a support member comprised of a cellulose acetate material. A film of cellulose acetate (Millipore) is first immersed in isopropanol to wet the membrane. The film is then immersed in a solution of 1% polyvinyl alcohol (PVA) (Sigma) for about 5 min to allow adsorption of the PVA. Next, the film is rinsed in deionized water for about 10 min. Lastly, the film is immersed in a solution of about 5% glutaraldehyde and about 1% HCl for about 20 minutes to cross-link the PVA in situ. The resulting film construction is expected to be a cellulose acetate support member having a first layer formed thereon.

Example 35

This example illustrates the immobilization of a bioactive species in the form of peptides to a film construction of the present invention as described in Example 30. The film of Example 30 is treated additionally according to Example 10 to place a second layer thereon. The film is then immobilized with the bioactive peptide Gly-Arg-Gly-Asp-Ser according to Example 18. The resulting film construction is expected to be a polycarbonate support member having the bioactive species Gly-Arg-Gly-Asp-Ser immobilized thereto.

Example 36

This example illustrates the immobilization of a bioactive species in the form of peptides to a film construction of the present invention as described in Example 31. The film of Example 31 is treated additionally according to Example 10 to place a second layer thereon. The film is then immobilized with the bioactive peptide Gly-Arg-Gly-Asp-Ser according to Example 18. The resulting film construction is expected to be a polyethylene support member having the bioactive species Gly-Arg-Gly-Asp-Ser immobilized thereto.

Example 37

This example illustrates the immobilization of a bioactive species in the form of peptides to a film construction of the present invention as described in Example 32. The film of Example 32 is treated additionally according to Example 10 to place a second layer thereon. The film is then immobilized with the bioactive peptide Gly-Arg-Gly-Asp-Ser according to Example 18. The resulting film construction is expected to be a polyvinylidenefluoride support member having the bioactive species Gly-Arg-Gly-Asp-Ser immobilized thereto.

Example 38

This example illustrates the immobilization of a bioactive species in the form of peptides to a film construction of the present invention as described in Example 33. The film of Example 33 is treated additionally according to Example 10 to place a second layer thereon. The film is then immobilized with the bioactive peptide Gly-Arg-Gly-Asp-Ser according to Example 18. The resulting film construction is expected to be a silver metal support member having the bioactive species Gly-Arg-Gly-Asp-Ser immobilized thereto.

Example 39

This example illustrates the immobilization of a bioactive species in the form of peptides to a film construction of the present invention as described in Example 34. The film of Example 34 is treated additionally according to Example 10 to place a second layer thereon. The film is then immobilized with the bioactive peptide Gly-Arg-Gly-Asp-Ser according to Example 18. The resulting film construction is expected to be a cellulose acetate support member having the bioactive species Gly-Arg-Gly-Asp-Ser immobilized thereto.

Example 40

This example illustrates the immobilization of a bioactive species in the form of cells to a film construction of the present invention as described in Example 36. Cells are seeded on the membrane of Example 36 according to Example 22. The expected results show that the film construction of Example 36 supports the immobilization of cells, while the unmodified polypropylene films are expected to be unable to support the immobilization of cells.

Example 41

This example illustrates the present invention having a support member comprised of an expanded polytetrafluoroethylene (ePTFE) covered stent in the form of a composite. To construct the composite, a nitinol wire stent is covered with an ePTFE tube. Once constructed, the composite device is immersed in isopropyl alcohol to prewet the ePTFE. This is followed by immersion in a solution of about 1% polyvinyl alcohol (PVA) (Sigma) in distilled water (w/v) for about 5 minutes followed by a washing in distilled water for about 10 minutes to remove unadsorbed bulk copolymer. The adsorbed PVA is cross-linked according to that detailed in Example 6 to form a first layer on the ePTFE support member component of the stent composite. A second layer is then applied to the first layer using the procedure illustrated in Example 12. The amine groups now immobilized on the ePTFE support member are linked via aldehyde cross-linking to a desired bioactive species. The resulting construction is expected to have a second layer attached to the first with bioactive species immobilized thereon.

Example 42

This example describes a method for the detection of the degree of cross-linking of the PVA. Fourier Transform Infrared Spectroscopy is used to detect the free hydroxyl groups before and after cross-linking. A shift in the hydroxyl group (OH) peak position from approximately 3349 $cm^{-1}$ to approximately 3383 $cm^{-1}$ with a decrease in peak height is proportional to the degree of cross-linking. A decrease in the height of the peak of about 50% and a shift from approximately 3349 $cm^{-1}$ to approximately 3383 $cm^{-1}$ is expected when about 50% of the hydroxyl groups of the PVA are cross-linked.

Example 43

This example illustrates a method for the detection of excessive cross-linking of the of a first layer comprised of polyvinyl alcohol (PVA) in an article of the present invention. In the method, a first article was prepared according to Example 6. A second article was also made using a glutaraldehyde/HCl exposure of only 5 minutes. Both articles were steam sterilized and examined using FTIR. The article made according to Example 6 revealed a broad peak at about 1690 $cm^{-1}$ and a sharp peak at about 1590 $cm^{-1}$. These peaks are believed to represent excess aldehyde groups present on the first layer and its partial hydrolysis products from steam exposure. The article that was exposed to glutaraldehyde/HCl for 5 minutes showed a small peak at about 1690 $cm^-$ and no peak at about 1590 $cm^{-1}$. These results demonstrate that the PVA layer of the second article was cross-linked to a lesser extent than the PVA layer of the first article. Accordingly, an increase in the peak areas at about 1690 $cm^-$ and 1590 $cm^-$ is indicative of the extent of cross-linking of the first layer of an article of the present invention.

Example 44

This example illustrates a method for detecting the presence of a second layer of PVA attached to a first layer of PVA in an article of the present invention. In the method, an article constructed according to Example 10 was steam sterilized and examined using FTIR. Strong peaks at about 2950 $cm^-$ and about 3350 $cm^-$ was seen under FTIR analysis. These peaks represent signals from the hydrocarbon backbone and the hydroxyl groups of the PVA, respectively, of the first and second layers. Peaks at 1590 $cm^-$ and 1690 $cm^-$ were not seen. The absence of peaks at 1590 $cm^-$ and 1690 $cm^-$ indicate that substantially all of the aldehyde groups from the cross-linking agent were consumed during the attachment of the second layer to the first layer. Accordingly, the ratio of peak area at about 2950 $cm^-$ to the peak area at about 1590 $cm^-$ is indicative of the extent to which excess, unreacted, aldehyde groups are present following attachment of a second layer to a first layer in the present invention.

Example 45

This example illustrates a method for detecting the presence of a second layer comprised of poly(lysine) attached to a first layer of PVA. In the method, an article made according to Example 12 was steam sterilized and examined using FTIR. A strong peak at about 2950 $cm^-$ was seen under FTIR analysis. This peak represents a signal from the hydrocarbon backbone of PVA of the first layer. A peak at about 1590 $cm^-$ was not observed. The absence of a peak at 1590 $cm^-$ indicates that substantially all of the aldehyde groups of the cross-linking agent of the first layer were consumed during the attachment of the second layer to the first layer. A peak at about 1650 $cm^-$ was observed. This peak represents a signal from the amide groups of the poly(lysine) moieties of the second layer. As in Example 44, the ratio of peak area at about 2950 $cm^-$ to the peak area at about 1590 $cm^-$ is indicative of the extent to which excess, unreacted, aldehyde groups are present following attachment of a second layer to a first layer in the present invention.

What is claimed is:

1. A material having bioactive species immobilized thereto, said material comprising:
   a support member;
   a first layer comprised of at least one species of a polymeric surfactant non-covalently attached to the support member, wherein the polymeric surfactant is a different chemical species than the support member, wherein the polymeric surfactant is cross-linked to itself in situ with a cross-linking agent; and
   at least one type of bioactive species attached to the cross-linking agent.

2. The material of claim 1 wherein the support member comprises a non-porous polymer material.

3. The material of claim 2 wherein the non-porous polymer material is selected from a member of the group consisting of polytetrafluoroethylene, polyethylene, polypropylene, polyethyleneterephthalate, polystyrene, polysulfone, polycarbonate, and regenerated cellulose.

4. The material of claim 1 wherein the support member comprises a porous polymer material.

5. The material of claim 4 wherein the porous polymer material is selected from a member of the group consisting of porous polytetrafluoroethylene, porous polyethylene, porous polypropylene, porous polyethyleneterephthalate, porous polyurethane, porous silicone rubber, porous polystyrene, porous polysulfone, porous polyester, porous polyhydroxyacids, porous polycarbonate, porous polyimide, porous polyamide, porous polyamino acids, and porous regenerated cellulose.

6. The material of claim I wherein the polymeric surfactant comprises a multifunctional copolymer comprised of at least one domain having a physicochemical affinity for the support member and at least one domain that is chemically reactive with the cross-linking agent.

7. The material of claim 1 wherein a spacer compound is interposed between the first layer and the bioactive species.

8. The material of claim 7 wherein the spacer compound is selected from a member of a group consisting of succinic acid, diaminohexane, glyoxylic acid, short chain polyethylene glycol, and glycine.

9. The material of claim 7 wherein the spacer compound is cleavable.

10. The material of claim 9 wherein the cleavable spacer compound is selected from the group consisting of polyhydroxyacids, polyanhydrides, polyamino acids, tartarates, and cysteine-linkers.

11. A material having immobilized bioactive species comprising:

a hydrophobic support member;
a first layer comprised of at least one species of a polymeric surfactant non-covalently attached to the support member and cross-linked to itself in situ with a cross-linking agent; and
    at least one type of bioactive species attached to the cross-linking agent.

12. The material of claim 11 wherein the polymeric surfactant comprises a multifunctional copolymer comprised of at least one domain having a physicochemical affinity for the support member and at least one domain that is chemically reactive with the cross-linking agent.

13. The material of claim 11 wherein a spacer compound is interposed between the first layer and the bioactive species.

14. The material of claim 13 wherein the spacer compound is selected from a member of a group consisting of succinic acid, diaminohexane, glyoxylic acid, short chain polyethylene glycol, and glycine.

15. The material of claim 13 wherein the spacer compound is cleavable.

16. The material of claim 15 wherein the cleavable spacer compound is selected from the group consisting of polyhydroxyacids, polyanhydrides, polyamino acids, tartarates, and cysteine-linkers.

17. A material for immobilization of bioactive species thereto, said material comprising:

a support member;
a first layer comprising at least one species of a polymeric surfactant non-covalently attached to the support member, wherein the polymeric surfactant is a different chemical species than the support member, and wherein the polymeric surfactant is cross-linked to itself in situ; and
a second layer comprising at least one species of a hydrophilic polymer covalently attached to the first layer, wherein the second layer has chemically reactive moieties for attaching bioactive species thereto.

18. The material of claim 17 wherein the support member comprises a non-porous polymer material.

19. The material of claim 18 wherein the non-porous polymer material is selected from a member of the group consisting of polytetrafluoroethylene, polyethylene, polypropylene, polyethyleneterephthalate, polystyrene, polysulfone, polycarbonate, polyethylene-co-vinyl acetate, polyamide, polyurethane, and regenerated cellulose.

20. The material of claim 17 wherein the support member is selected from a member of the group consisting of silk, wool, and leather.

21. The material of claim 17 wherein the support member comprises a porous polymer material.

22. The material of claim 21 wherein the porous polymer material is selected from a member of the group consisting of porous polytetrafluoroethylene, porous polyethylene, porous polypropylene, porous polyethyleneterephthalate, porous polyurethane, porous silicone rubber, porous polystyrene, porous polysulfone, porous polyester, porous polyhydroxyacids, porous polycarbonate, porous polyimide, porous polyamide, porous polyamino acids, and porous regenerated cellulose.

23. The material of claim 17 wherein the polymeric surfactant comprises a multifunctional copolymer comprised of at least one domain having a physicochemical affinity for the support member and at least one domain that is chemically reactive with a cross-linking agent.

24. The material of claim 17 wherein the hydrophilic polymer comprises chemically functional groups to which the first layer is covalently attached and additional chemically functional groups to which bioactive species can be attached.

25. The material of claim 17 wherein the polymeric surfactant of the first layer is selected from the group consisting of polyvinyl alcohol, polyethylene glycol, polypropylene glycol, dextran, agarose, alginate, polyacrylamide, polyglycidol, poly(vinyl alcohol-co-ethylene), poly(ethyleneglycolco-propyleneglycol), poly (vinyl acetate-co-vinyl alcohol), poly(tetrafluoroethylene-co-vinyl alcohol), poly(acrylonitrile-co-acrylamide), poly (acrylonitrile-co-acrylic acid-co-acrylamidine), polyacrylic acid, poly-lysine, polyethyleneimine, polyvinyl pyrrolidone, polyhydroxyethylmethacrylate, and polysulfone, and their copolymers, either alone or in combination.

26. The material of claim 17 wherein the hydrophilic polymer of the second layer is selected from the group consisting of polyvinyl alcohol, polylysine, poly (acrylonitrile-co-acrylic acidacrylamidine), polyacrylic acid, polyhydroxyethylmethacrylate, polyvinylpyrrolidone, polyethylene glycol, alginate, sepharose, agarose, polyethyleneimine, polyallylamine, polyaminoethylmethacrylate, polyornithine, polyaminoacrylamide, polyacrylamide, polyacrolein, polyacryloxysuccinimide, polysulfone, poly(acrylonitrile-co-acrylamide), and their copolymers, either alone or in combination.

27. The material of claim 17 wherein the hydrophilic polymer comprises a random copolymer of tetrafluoroethylene and vinyl alcohol.

28. The material of claim 17 wherein the hydrophilic polymer comprises a copolymer of hydroxyethylmethacrylate and hexafluoroacrylate.

29. The material of claim 17 wherein the hydrophilic polymer comprises a copolymer of polyethylene and vinyl alcohol.

30. The material of claim 17 further comprising a spacer compound for interposition between the second layer and a bioactive species.

31. The material of claim 30 wherein the spacer compound is selected from a member of a group consisting of succinic acid, diaminohexane, glyoxylic acid, short chain polyethylene glycol, and glycine.

32. The material of claim 14 wherein the spacer compound is cleavable.

33. The material of claim 16 wherein the cleavable spacer compound is selected from the group consisting of polyhydroxyacids, polyanhydrides, polyamino acids, tartarates, and cysteine-linkers.

* * * * *